US012788518B2

(12) United States Patent
Cordasco

(10) Patent No.: US 12,788,518 B2
(45) Date of Patent: Nov. 10, 2026

(54) ROBOTIC SYSTEMS, DEVICES AND METHODS FOR PERFORMING DENTAL PROCEDURES ON PATIENTS

(71) Applicant: John A. Cordasco, Dover, NJ (US)

(72) Inventor: John A. Cordasco, Dover, NJ (US)

( * ) Notice: Subject to any disclaimer, the term of this patent is extended or adjusted under 35 U.S.C. 154(b) by 203 days.

(21) Appl. No.: 18/397,306

(22) Filed: Dec. 27, 2023

(65) Prior Publication Data

US 2024/0122665 A1 Apr. 18, 2024

Related U.S. Application Data

(63) Continuation of application No. 17/007,187, filed on Aug. 31, 2020, now Pat. No. 11,890,071.

(51) Int. Cl.

| | |
|---|---|
| ***A61B 34/00*** | (2016.01) |
| ***A61B 34/37*** | (2016.01) |
| ***A61B 90/00*** | (2016.01) |
| ***A61B 90/30*** | (2016.01) |
| ***A61B 90/57*** | (2016.01) |
| ***A61C 3/02*** | (2006.01) |
| ***B25J 9/04*** | (2006.01) |
| ***B25J 9/10*** | (2006.01) |

(52) U.S. Cl.

CPC .............. *A61B 34/70* (2016.02); *A61B 34/37* (2016.02); *A61B 90/30* (2016.02); *A61B 90/361* (2016.02); *A61B 90/37* (2016.02); *A61B 90/57* (2016.02); *A61C 3/02* (2013.01); *B25J 9/04* (2013.01); *B25J 9/106* (2013.01)

(58) Field of Classification Search

CPC ......... A61B 34/00; A61B 34/37; A61B 34/70; A61B 90/00; A61B 90/30; A61B 90/57; A61B 90/361; B25J 9/106

See application file for complete search history.

(56) References Cited

U.S. PATENT DOCUMENTS 5,562,448 A * 10/1996 Mushabac .......... A61C 13/0004 433/215

2017/0360521 A1* 12/2017 Johnson ................. A61B 90/50

* cited by examiner

*Primary Examiner* — Vi X Nguyen

(74) *Attorney, Agent, or Firm* — Charney IP Law LLC

(57) ABSTRACT

A system for performing a dental procedure includes a hand piece having a robot arm that extends along a first axis, and a medical tool coupled with a distal end of the robot arm. The system includes a first gimbal coupled with the robot arm for rotating the robot arm and the medical tool about the first axis, a second gimbal coupled with the robot arm for tilting the medical tool up and down relative to the first axis, and a third gimbal coupled with the robot arm for moving the medical tool up and down along a second axis that is perpendicular to the first axis.

18 Claims, 23 Drawing Sheets

ROBOTIC SYSTEMS, DEVICES AND METHODS FOR PERFORMING DENTAL PROCEDURES ON PATIENTS

CROSS-REFERENCE TO RELATED APPLICATIONS

The present patent application is a continuation application of U.S. patent application Ser. No. 17/007,187, filed Aug. 31, 2020, the disclosure of which is hereby incorporated by reference herein.

BACKGROUND OF THE INVENTION

Field of the Invention

The present patent application is generally related to dentistry, and is more specifically related to robotic systems, devices and methods for performing dental procedures on patients.

Description of the Related Art

Dental procedures are typically performed manually whereby the dentist manipulates surgical tools for performing complex surgical and restoration procedures. Dental procedures can also be performed using a variety of supportive technologies that augment the dentists ability to examine and treat the patient.

Dentists rely of their medical expertise, manual dexterity, and hand-eye coordination to successfully complete dental procedures. Skill levels and expertise vary widely among dental professionals so that the results of procedures are not always equivalent. To improve the success rate of a procedure, dentists often use data from observation, physical tests, and detectable characteristics. For example, X-rays provide visual details that are usually unavailable to the naked eye. Such data helps the dentist to use his or her best judgment to decide on a treatment approach that is well-suited for the patient.

There have been some efforts directed to using technology for automating dental procedures. For example, U.S. Pat. No. 9,675,419 to Akeel et al., the disclosure of which is hereby incorporated herein, teaches a system and a method for automating a medical process including providing a memory for storing a software program, a computer connected to the memory for running the software program, a display connected to the computer for generating a visual representation of output data generated by the computer running the program, a user interface connected to the computer for obtaining image data representing a configuration of a patient treatment space and fixed markers in the treatment space and storing the image data in the memory, a robot arm connected to the computer, and a medical tool mounted on the robot arm, whereby when a human inputs a selected treatment procedure into the computer, the computer runs the software program to generate a tool path based upon the treatment procedure and the image data, and the computer operates the robot arm to move the medical tool along the tool path without human guidance, and whereby the data generated during the treatment procedure is stored, analyzed, and shared among collaborating computer systems.

In spite of the above advances, there is a need for improved robotic systems, devices and methods for performing dental procedures on patients.

There also remains a need for improved systems for completing dental procedures that may be remotely controlled by medical personnel, such as dentists.

SUMMARY OF THE INVENTION

In one embodiment, a system for performing a dental procedure preferably includes a hand piece having a robot arm that extends along a first axis, and a medical tool coupled with a distal end of the robot arm.

In one embodiment, the hand piece desirably includes a first gimbal coupled with the robot arm for rotating the robot arm and the medical tool about the first axis.

In one embodiment, the hand piece desirably includes a second gimbal coupled with the robot arm for tilting the medical tool up and down (e.g., adjusting the angle) relative to the first axis.

In one embodiment, the hand piece desirably includes a third gimbal coupled with the robot arm for moving the medical tool up and down along a second axis (e.g., a vertical axis) that is perpendicular to the first axis.

In one embodiment, the robot arm preferably includes a first shaft that extends along the first axis.

In one embodiment, the hand piece preferably has a linkage for extending and retracting the first shaft of the robot arm along the first axis.

In one embodiment, the first shaft preferably includes a first conduit that extends along the first axis from a proximal end to a distal end of the first shaft.

In one embodiment, the robot arm desirably includes a second shaft that is disposed within the first conduit of the first shaft and that extends along the first axis. In one embodiment, the second gimbal is desirably coupled with the second shaft.

In one embodiment, the second shaft preferably has a second conduit that extends along the first axis from a proximal end to a distal end of the second shaft.

In one embodiment, the robot arm preferably includes a third shaft that is disposed within the second conduit and that extends along the first axis.

In one embodiment, the third gimbal is coupled with the third shaft.

In one embodiment, the hand piece desirably includes a turret that is configured to rotate within a plane (e.g., a horizontal plane) that is perpendicular to the second axis (e.g., a vertical plane).

In one embodiment, the robot arm is mounted atop the turret and rotates simultaneously with the turret In one embodiment, the hand piece desirably includes a panning linkage coupled with the turret for moving the turret and the robot arm left and right within the plane, which, in turn, moves the medical tool left and right.

In one embodiment, the first, second and third shafts have respective distal ends that are coupled with the medical tool (e.g., a dental drill).

In one embodiment, the hand piece preferably includes a first motor that is coupled with the first shaft for extending and retracting the first shaft along the first axis, which, in turn, extends and retracts the medical tool along the first axis.

In one embodiment, the hand piece preferably includes a second motor coupled with the first shaft for rotating the first shaft about the first axis, which, in turn, rotates and/or rolls the medical tool about the first axis.

In one embodiment, the hand piece preferably includes a third motor coupled with the panning linkage for moving the first shaft to the left and the right within the plane that is perpendicular to the second axis, which, in turn, moves the medical tool to the left and right.

In one embodiment, the system preferably includes a fourth motor coupled with the second shaft for extending and retracting the second shaft along the first axis, which, in turn, tilts the medical tool up and down.

In one embodiment, the system preferably includes a fifth motor coupled with the third shaft for extending and retracting the third shaft along the first axis, which, in turn, moves the medical tool up and down within a second axis that is perpendicular to the first axis.

In one embodiment, the medical tool desirably includes a dental drill having a rotatable cutting instrument, which may be used to perform a variety of common dental procedures, including removing decay, polishing fillings, performing cosmetic dentistry, and altering prostheses.

In one embodiment, the robot arm of the hand piece is preferably adapted to perform the following functions: 1) extend and retract the dental drill along a first axis; 2) roll and/or rotate the dental drill about the first axis; 3) tilt and/or adjust the angle of the dental drill relative to the first axis; 4) adjust the vertical height of the dental drill by moving the dental drill along a second axis (e.g., a vertical axis) that is perpendicular to the first axis; 5) move and/or rotate the dental drill to the left and right within a plane that is parallel with the first axis and perpendicular to the second axis.

In one embodiment, the hand piece may include at least one optical element secured to the medical tool for capturing images at a surgical site.

In one embodiment, the hand piece may include at least one light generating element secured to the medical tool for illuminating the surgical site.

In one embodiment, the hand piece is preferably in communication with a control system for operating and controlling the hand piece. In one embodiment, the control system may include a central processing unit, a memory, and a software application for operating the system, the hand piece, and the robot arm.

In one embodiment, the system desirably includes a manual controller in communication with the control system for controlling movement of the robot arm. An operator may engage the manual controller for moving the robot arm and orienting the medical tool secured to the distal end of the robot arm. The manual controller may include one or more joy sticks or paddles that are engaged by an operator (e.g., a dentist) for remotely moving the robot arm and the medical tool coupled with the distal end of the robot arm.

In one embodiment, the system may include a display monitor in communication with the at least one optical element for displaying the images captured by the at least one optical element.

In one embodiment, the system preferably includes an anchoring assembly that is adapted for being secured to a patient.

In one embodiment, the hand piece is mounted on the anchoring assembly for positioning the hand piece and the medical tool at the surgical site.

In one embodiment, the anchoring assembly preferably includes a clamp support arm having a distal end that is adapted for being inserted into a patient's mouth.

In one embodiment, the anchoring assembly preferably includes one or more tooth clamps coupled with the clamp support arm for clamping onto teeth inside the patient's mouth.

In one embodiment, the anchoring assembly may have a tongue protector inserted into the patients mouth. In one embodiment, the tongue protector is positioned between the patients tongue and the medical tool coupled with the distal end of the robot arm.

In one embodiment, the anchoring assembly may include a chin clamp adapted to engage the patients chin for providing a clamping force between the one or more tooth clamps and the chin clamp.

In one embodiment, a system for performing a dental procedure preferably includes a hand piece including a robot arm that extends along a first axis, and a dental drill having a rotatable cutting instrument coupled with a distal end of the robot arm.

In one embodiment, the hand piece may include a first gimbal coupled with the robot arm for rotating the dental drill about the first axis of the robot arm.

In one embodiment, the hand piece may include a second gimbal coupled with the robot arm for tilting and/or adjusting the angle of the dental drill relative to the first axis.

In one embodiment, the hand piece may include a third gimbal coupled with the robot arm for moving the dental drill up and down along a second axis (e.g., a vertical axis) that is perpendicular to the first axis. In one embodiment, the third gimbal may be used for adjusting the height of the medical tool relative to a patient.

In one embodiment, the system preferably includes an anchoring assembly configured to support the hand piece at the surgical site.

In one embodiment, the anchoring assembly preferably includes a clamp support arm having a distal end adapted for being inserted into a patient's mouth.

In one embodiment, the anchoring assembly preferably includes one or more tooth clamps coupled with the clamp support arm for clamping onto teeth inside the patients mouth.

In one embodiment, the anchoring assembly preferably includes a tongue protector positioned between the patient's tongue and the dental drill.

In one embodiment, the anchoring assembly preferably includes a chin clamp adapted to engage the patient's chin for providing a clamping force between the one or more tooth clamps and the chin clamp.

In one embodiment, the hand piece desirably includes at least one optical element secured to the dental drill for capturing images at a surgical site.

In one embodiment, the hand piece may have at least one light generating element (e.g., a light emitting diode) for illuminating the surgical site.

In one embodiment, the system may include a control system having a central processing unit, a memory, and a software application for operating the robot arm.

In one embodiment, the system may include a manual controller in communication with the control system for controlling movement of the robot arm.

In one embodiment, the system may have a display monitor in communication with the at least one optical element for displaying the images captured by the at least one optical element.

In one embodiment, the robot arm preferably has a first shaft having a first conduit that extends along the first axis, a second shaft that is disposed within the first conduit of the first shaft and that extends along the first axis, the second shaft having a second conduit that extends along the first axis, and a third shaft that is disposed within the second conduit of the second shaft.

In one embodiment, the hand piece preferably has a linkage for extending and retracting the first shaft of the robot arm along the first axis.

In one embodiment, the second gimbal is coupled with the second shaft.

In one embodiment, the third gimbal is coupled with the third shaft.

In one embodiment, the hand piece preferably includes a first motor coupled with the first shaft for extending and retracting the first shaft along the first axis, a second motor coupled with the first shaft for rotating the first shaft around the first axis, a third motor coupled with a panning linkage for moving the first shaft left and right within a plane that is parallel with the first axis, a fourth motor coupled with the second shaft for extending and retracting the second shaft along the first axis, and a fifth motor coupled with the third shaft for extending and retracting the third shaft along the first axis.

DETAILED DESCRIPTION OF PREFERRED EMBODIMENTS

Figure 1A:
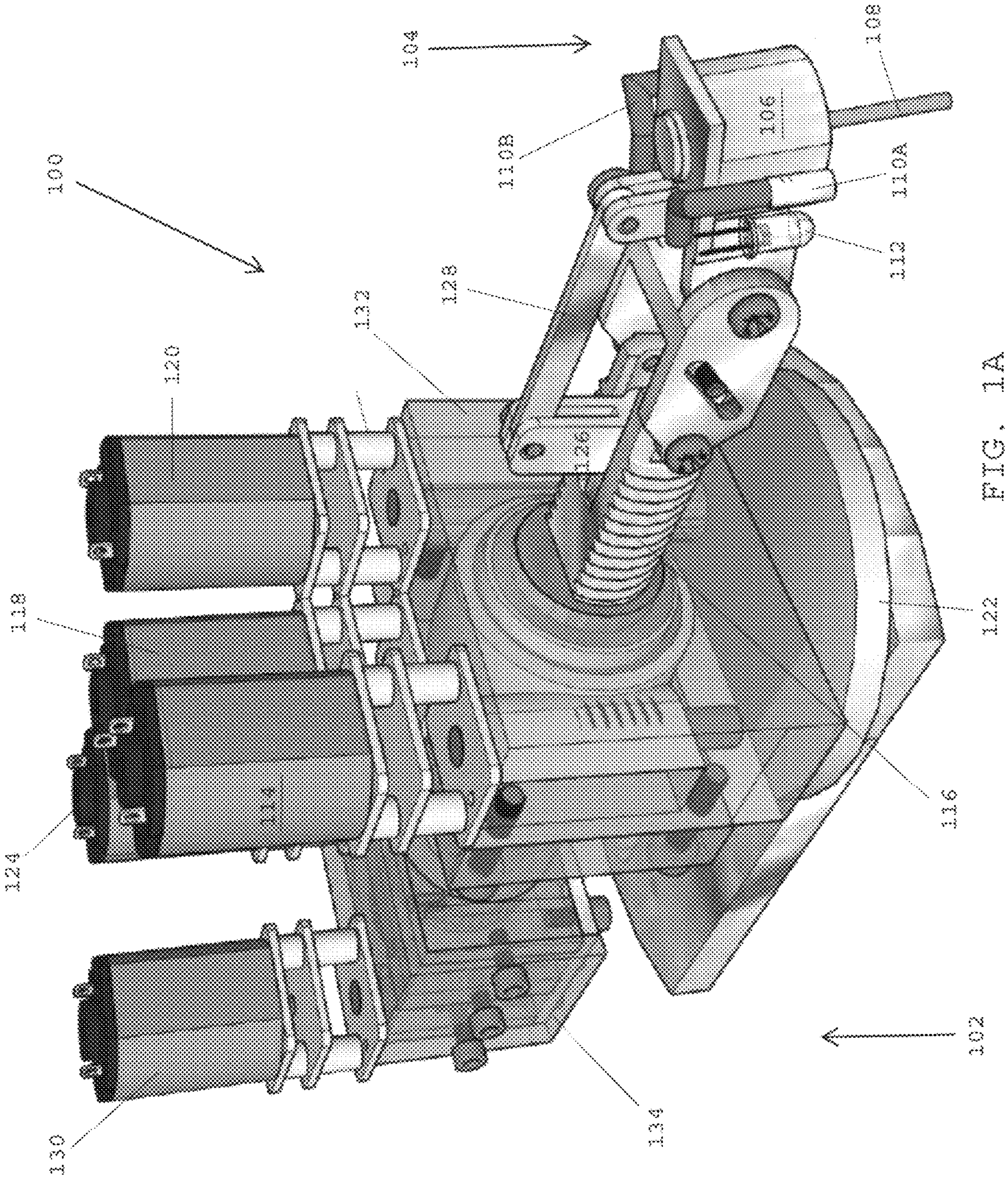
FIG. 1A is a perspective view of a hand piece of a robotic system for performing dental procedures, in accordance with one embodiment of the present patent application.

Referring to FIGS. 1A-1D, in one embodiment, a robotic system for performing a dental procedure preferably includes a hand piece 100 that may be remotely controlled by an operator (e.g., a dentist). In one embodiment, the hand piece 100 preferably has a proximal end 102 and a distal end 104. In one embodiment, the hand piece 100 preferably includes a turbine housing 106 that is located at the distal end 104 of the hand piece, and a drill bit 108 that projects downwardly from an underside of the turbine housing 106. In one embodiment, the turbine housing 106 is desirably powered for rotating the drill bit 108 for drilling teeth. In one embodiment, the turbine housing 106 may be powered by compressed air.

In one embodiment, the hand piece 100 preferably includes components for providing medical personnel with visibility at the distal end 104 of the hand piece. In one embodiment, the hand piece 100 may include first and second optic tubes 110A, 110B that provide visibility for medical personnel (e.g., a dentist) at a surgical site adjacent the distal end 104 of the hand piece. In one embodiment, the robotic system may include one or more monitors (e.g., video monitors; computer screens) for displaying still or moving pictures that are captured by the first and second optic tubes 110A, 110B. In one embodiment, the hand piece 100 preferably includes one or more light emitting diodes (LEDs) for illuminating a surgical site at the distal end 104 of the hand piece, or in the field of view of the first and second optic tubes 110A, 110B.

In one embodiment, the hand piece 100 preferably includes a series of gears, shafts, and/or linkages that may be moved for enabling the turbine housing 106 to be extended, retracted, moved up and down (i.e., vertical movement), angulated up and down (i.e., tilting movement), rotated about an axis (i.e., rolling movement), and turned to the left and right (i.e., panning movement). In one embodiment, the hand piece 100 may include an at least three axis gimbal linkage or structure for enabling the tilting, rolling, and panning movement of the turbine housing 106. In one embodiment, the robotic system may include one or more motors that are coupled with the gears, shafts, and/or linkages for selectively moving the turbine housing 106.

In one embodiment, the hand piece 100 preferably includes a first shaft 116 that may be extended and retracted along a longitudinal axis $A_1$ (FIG. 1B) of the first shaft for selectively extending and retracting the turbine housing 106. In one embodiment, the hand piece 100 preferably includes an at least three axis gimbal linkage for controlling the vertical position, tilt, pan, and roll of the turbine housing 106 at the distal end of the first shaft. In one embodiment, the at least three axis gimbal linkage controls the vertical position, the tilt (i.e., up and down angle), the pan (e.g., left and right movement), and the roll (i.e., rotation about the longitudinal axis of the first shaft) at the distal end of the turbine housing. As a result of the extendable and retractable first shaft 116 and the at least three axis gimbal linkage provided at the distal end of the first shaft, the turbine housing 106 of the hand piece 100 may be extended and retracted along the longitudinal axis $A_1$ of the first shaft, moved up and down along a vertical axis $A_2$ (FIG. 1B) that is perpendicular to the longitudinal axis $A_1$ (FIG. 1B) of the first shaft, angulated up and down (i.e., tilt) at the distal end of the first shaft, panned to the left and right at the distal end of the first shaft, and rolled (i.e., rotated) about the longitudinal axis of the first shaft.

The various movements of the turbine housing 106 preferably enable the drill bit 108 to be moved into different positions and orientations for performing a dental procedure such as drilling teeth. In one embodiment, the different movements of the turbine housing may be controlled remotely using one or more central processing units and manual controllers such as joy sticks or control paddles.

In one embodiment, the hand piece 100 of the robotic system preferably includes a first motor 114 that is adapted to extend and retract the first shaft, which, in turn, extends and retracts the turbine housing 106 at the distal end 104 of the hand piece.

In one embodiment, the hand piece 100 preferably includes a second motor 118 that is adapted to rotate (i.e., roll) the first shaft 116 about its longitudinal axis for selectively rotating and/or rolling the turbine housing 106 about the longitudinal axis $A_1$ (FIG. 1B) of the first shaft.

In one embodiment, the extension and retraction of the turbine housing 106 may be performed independently of the rolling of the turbine housing about the longitudinal axis $A_1$.

In one embodiment, the hand piece 100 preferably includes a third motor 120 that is coupled with a turret 122 via gears and linkages for selectively panning the first shaft 116 and the turbine housing 106 to the left and right. In one embodiment, the panning movement of the turbine housing 106 may be performed independently of the extension, retraction, and rolling of the first shaft 116 and the turbine housing 106.

In one embodiment, the hand piece 100 preferably includes a fourth motor 124 that is coupled with a second shaft 126 and a pivoting lever 128 for changing the angle (i.e., the tilt) of the turbine housing 106. In one embodiment, a distal end of the second shaft 126 is pivotally coupled with a proximal end of the pivoting lever 128 and a distal end of the pivoting lever 128 is pivotally coupled with a proximal end of the turbine housing 106 for changing the angle (i.e., the tilt) of the turbine housing 106 as the second shaft 126 is extended and retracted along the longitudinal axis $A_1$ of the first shaft 116.

In one embodiment, the fourth motor 124 is preferably activated for extending the second shaft 126, which, in turn, extends the pivoting lever 128 for pivoting the turbine housing 106 in a clockwise direction R1 (FIG. 1B) for changing the angle (i.e., tilt) of the turbine housing 106. In one embodiment, the fourth motor 124 may be activated for retracting the second shaft 126 toward the proximal end of the hand piece 100 for rotating the turbine housing 106 in a counter clockwise direction designated R2 (FIG. 1B) for changing the tilt of the turbine housing.

In one embodiment, the tilting of the turbine housing 106 may be performed independently of the extension and retraction of the turbine housing, the rolling of the turbine housing, and the panning of the turbine housing.

In one embodiment, the hand piece 100 preferably includes a fifth motor 130 that is coupled with a third shaft that is adapted to change the elevation or vertical height of the turbine housing 106 at the distal end of the hand piece. In one embodiment, when the third shaft is extended in a distal direction by the fifth motor 130, the turbine housing 106 is moved down in a vertical direction along the axis $A_2$ (FIG. 1B). In one embodiment, when the third shaft is retracted by the fifth motor 130, the turbine housing 106 moves up in a vertical direction along the axis $A_2$ (FIG. 1B). In one embodiment, the vertical height adjustments of the turbine housing 106 may be performed independently of the tilting of the turbine housing, the panning of the turbine housing, the extension and retraction of the turbine housing, and the rolling of the turbine housing.

In one embodiment, each of the vertical height adjustments, tilting, panning, extension and retraction, and rolling of the turbine housing may be performed independently of one another.

In one embodiment, the hand piece 100 preferably includes a forward housing 132 that may contain gears and/or linkages that are coupled with the respective first, second and third motors 114, 118, and 120. In one embodiment, the first, second and third motors 114, 118, and 120 may be mounted on the forward housing 132. In one embodiment, the forward housing 132 is mounted on the turret 122 and pans (i.e., moves left and right within a horizontal plane) simultaneously with the turret 122. In one embodiment, the first shaft 116 extends completely through the forward housing 132 so that the first shaft is located on both the proximal and distal sides of the forward housing 132.

In one embodiment, the hand piece 100 preferably includes a rear housing 134 that desirably contains gears and/or linkages coupled with the respective fourth and fifth motors 124, 130. In one embodiment, the fourth and fifth motors 124, 130 are preferably mounted on the rear housing 134. In one embodiment, the rear housing 134 is desirably coupled with a proximal end of the first shaft 116 and is adapted to move with the first shaft 116 as the first shaft moves distally (i.e., extends), proximally (i.e., retracts), and rotates (i.e., rolls) about the longitudinal axis $A_1$ (FIG. 1B) of the first shaft 116.

Figure 1B:
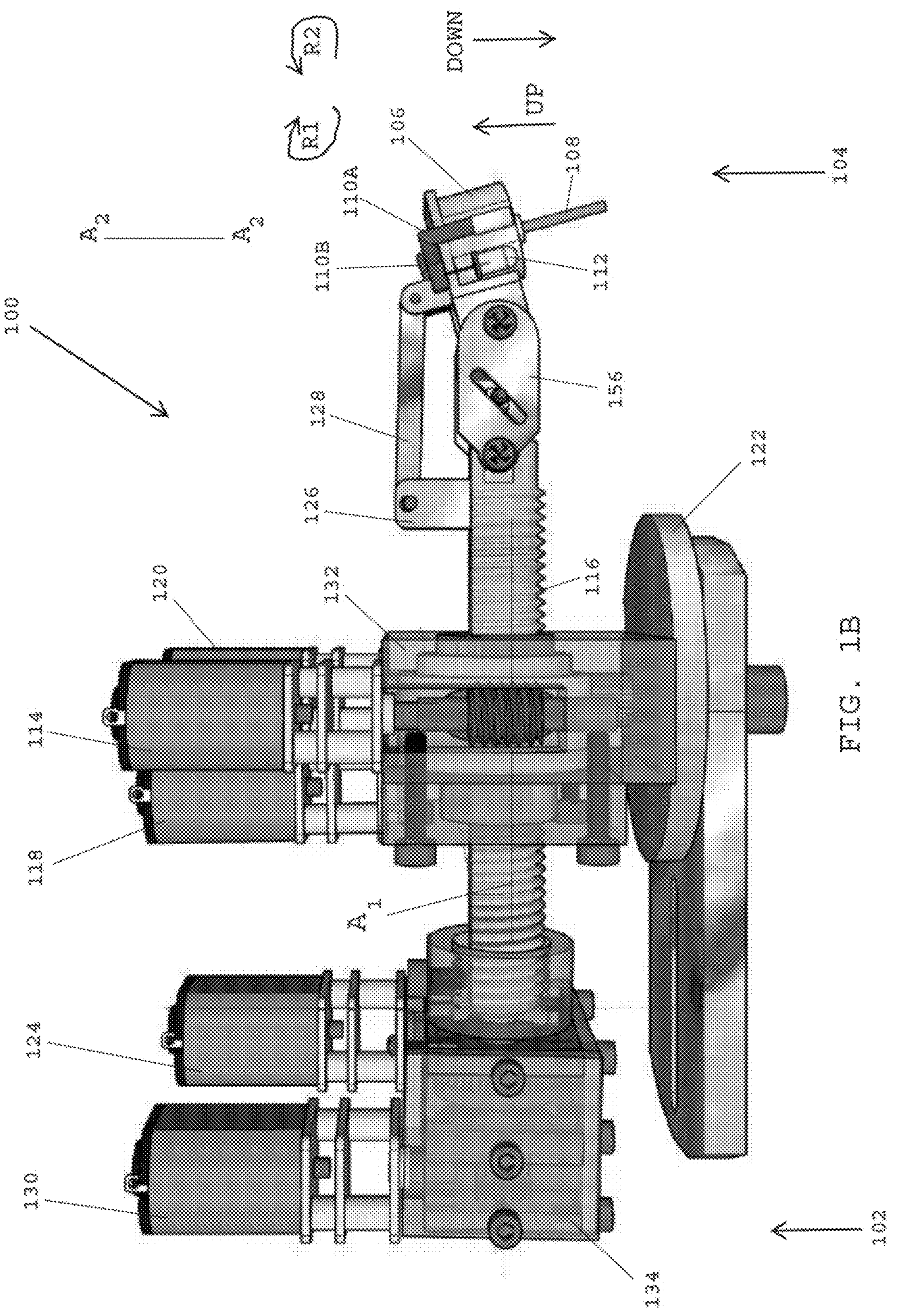
FIG. 1B is a right side view of the hand piece shown in FIG. 1A.
Figure 1C:
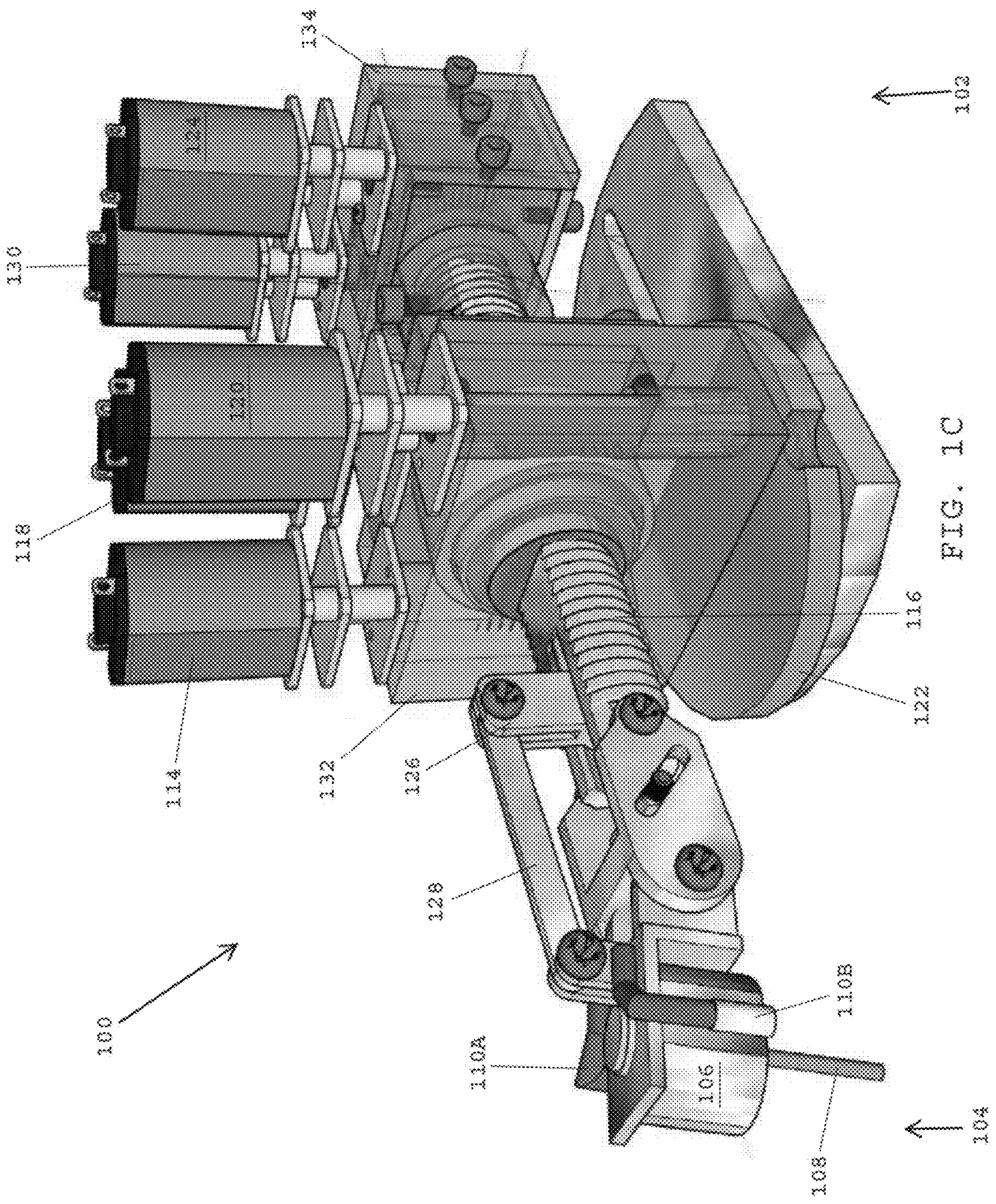
FIG. 1C is a perspective view of a distal end of the hand piece shown in FIGS. 1A and 1B.
Figure 1D:
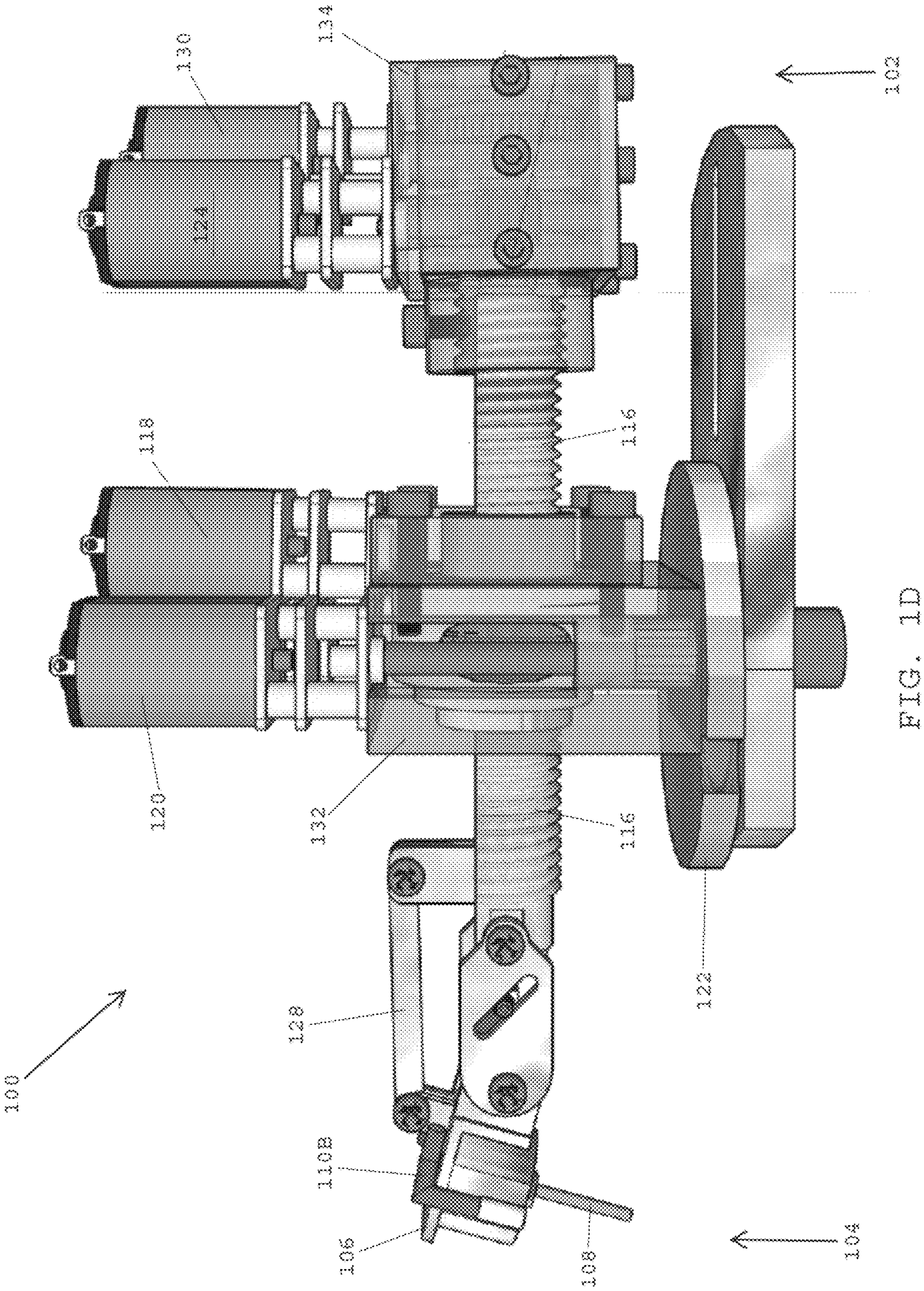
FIG. 1D is a left side view of the hand piece shown in FIGS. 1A-1C.
Figure 1E:
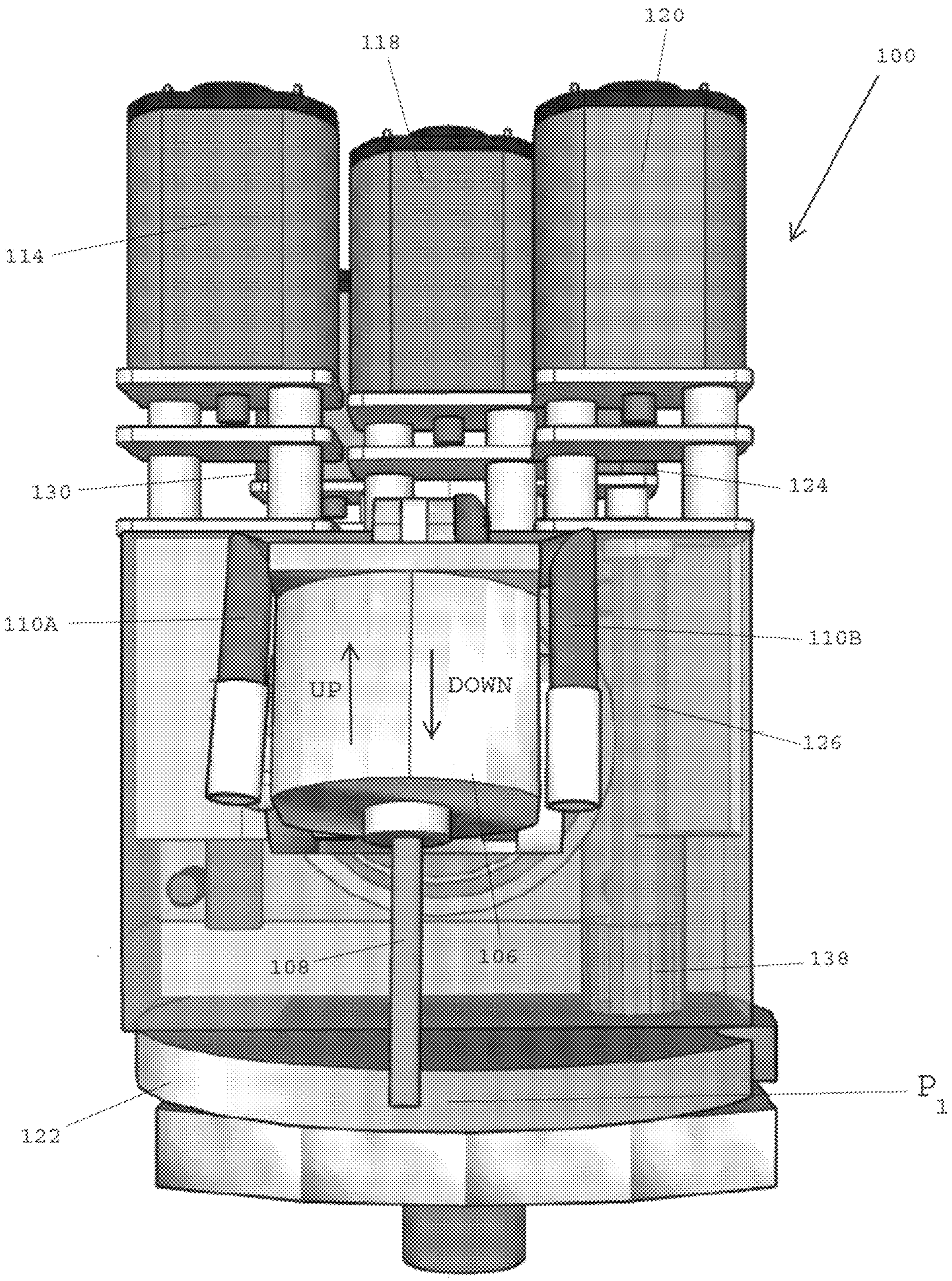
FIG. 1E is a distal end view of the hand piece shown in FIGS. 1A-1D.
Figure 1F:
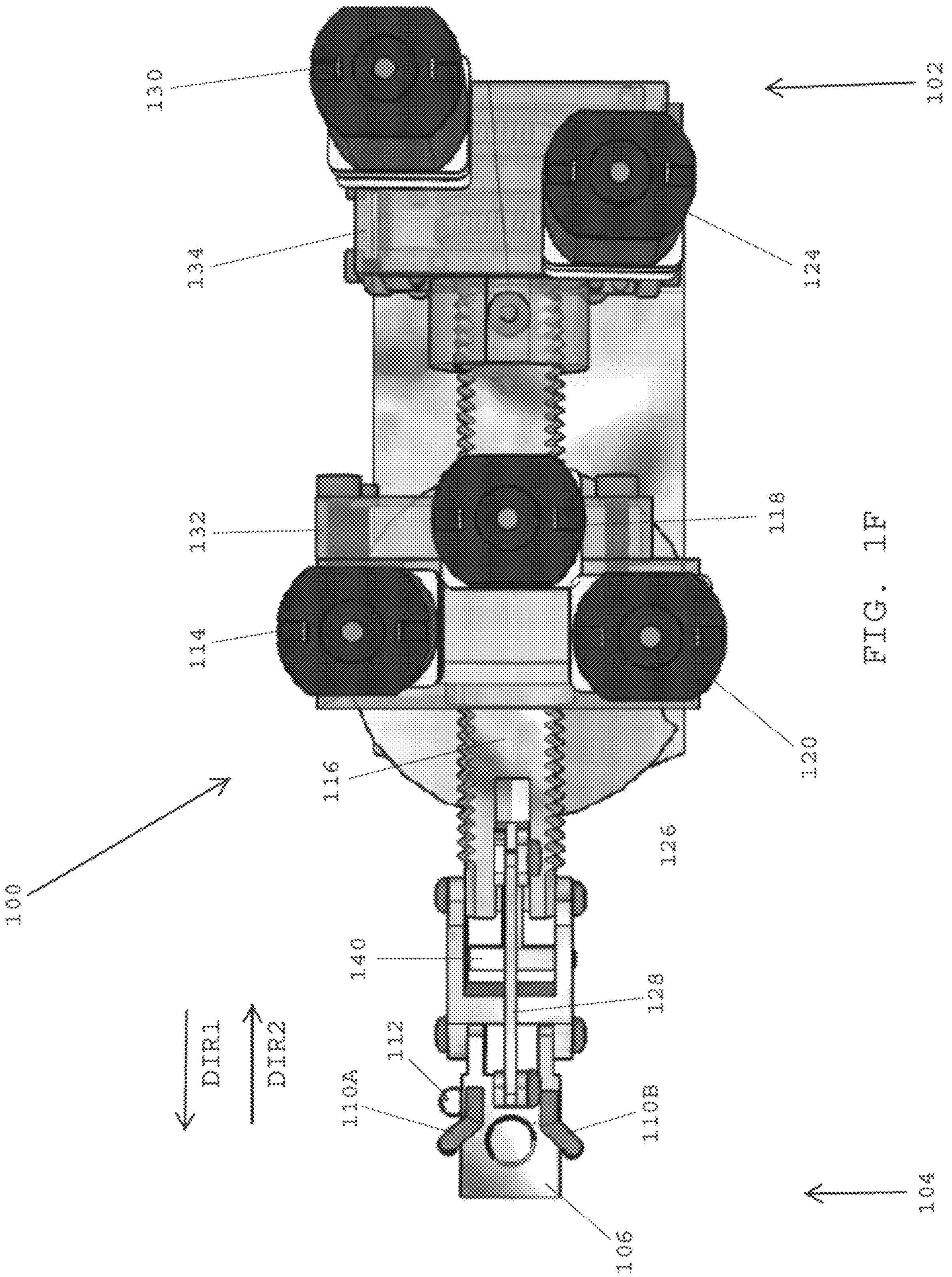
FIG. 1F is a top view of the hand piece shown in FIGS. 1A-1F.

Referring to FIGS. 1E and 1F, in one embodiment, the hand piece 100 preferably includes the first motor 114 that is coupled with the first shaft 116 for selectively extending and retracting the first shaft 116. Referring to FIG. 1F, in one embodiment, the first motor 114 moves in a first direction for extending the first shaft 116 distally in a direction designated DIR1.

In one embodiment, the first motor 114 moves in an opposite, second direction for retracting the first shaft 116 proximally in an opposite direction designated DIR2. In one embodiment, the turbine housing 106, which is coupled with the distal end of the first shaft 116, extends and retracts simultaneously with the first shaft 116. Thus, in one embodiment, the first motor 114 may be used to selectively extend and retract the turbine housing 106 and the drill bit 108 (FIG. 1E) that is secured to the turbine housing.

Referring to FIGS. 1E and 1F, in one embodiment, the hand piece 100 preferably includes the second motor 118 that is connected with the first shaft 116 via gears and/or linkages for selectively rotating the first shaft 116 about the longitudinal axis $A_1$ (FIG. 1F) of the first shaft 116. In one embodiment, the second motor 118 may be activated for rotating (i.e., rolling) the first shaft 116 about the longitudinal axis $A_1$ in a clockwise direction. In one embodiment, the second motor 118 may be reversed for rotating (i.e., rolling) the first shaft 116 about its longitudinal axis $A_1$ in a counterclockwise direction. Thus, the turbine housing 106 may be rotated (i.e., rolled) simultaneously with the first shaft 116 as the first shaft rolls in clockwise and counterclockwise directions.

In one embodiment, the hand piece 100 preferably includes the third motor 120 that is adapted to pan the turret 122 to the left and right. In one embodiment, the panning movement preferably takes place within a plane $P_1$ shown in FIG. 1E (e.g., a horizontal plane). In one embodiment, the hand piece 100 preferably includes a vertically extending shaft 136 having an upper end that is coupled with the third motor 120 and a lower end that includes a pinion gear 138 that engages gear teeth provided on the turret 122. In one embodiment, the third motor 120 may be moved in a first direction for rotating the vertical shaft 136 and the pinion gear 138, which, in turn, pans the turret 122 to the left (e.g., a counterclockwise rotation). In one embodiment, the third motor 120 may be activated and moved in an opposite direction for panning the turret 122 to the right (e.g., a clockwise rotation). Thus, by activating the third motor 120, the first shaft 116 and the turbine housing 106 secured to the distal end of the first shaft may be selectively panned to the left and right at the distal end 104 of the hand piece 100.

Referring to FIG. 1F, in one embodiment, the hand piece 100 preferably includes the fourth motor 124 that is coupled with the second shaft 126 for extending and retracting the second shaft along the longitudinal axis $A_1$. In one embodiment, as the second shaft 126 moves along the longitudinal axis $A_1$, the second shaft moves independently of the first shaft 116.

In one embodiment, the extension and retraction of the second shaft 126 along the longitudinal axis $A_1$ is adapted to change the angle (i.e., tilt) of the turbine housing 106 via a pivot lever 128 that extends from the distal end of the second shaft 126 to the proximal end of the turbine housing 106. In one embodiment, the fourth motor 124 is activated for extending the second shaft 126 relative to the first shaft 116, which rotates (i.e., tilts) the turbine housing 106 down. In one embodiment, the fourth motor 124 may be activated for retracting the second shaft 126 relative to the first shaft 116, which rotates (i.e., tilts) the turbine housing 106 up.

In one embodiment, the hand piece 100 preferably includes the fifth motor 130 that is coupled with a third shaft 140 that passes through the second shaft 126, which, in turn, passes through the first shaft 116. In one embodiment, the fifth motor 130 may be activated for extending the third shaft 140 in a distal direction, which, in turn, changes the vertical height of the turbine housing by moving the turbine housing 106 in the DOWN direction shown in FIG. 1F. In one embodiment, the fifth motor 130 may be activated for retracting the third shaft 140 in a proximal direction, which, in turn, changes the vertical height of the turbine housing by moving the turbine housing 106 in the UP direction shown in FIG. 1F.

Thus, the hand piece 100 preferably has various linkages including at least a three axis gimbal linkage which enables the turbine housing 106 to be selectively extended, retracted, rotated (i.e., rolled) about the longitudinal axis $A_1$ (FIG. 1B) of the first shaft 116, moved up and down (i.e., vertical adjustment), moved left and right (i.e., panning movement), and angulated up and down (i.e., tilting movement). In one embodiment, the hand piece 100 is preferably coupled with a one or more central processing units and one or more controllers (i.e., joysticks) that enable medical personnel to automatically adjust and control the exact position of the turbine housing 106 that is located at the distal end 104 of the hand piece 100.

In one embodiment, the first and second optic tubes 110A, 110B provide medical personnel with visibility at the distal end 104 of the hand piece 100 so that the medical personnel may view a surgical site (e.g., inside a patient's mouth). In one embodiment, the one or more LEDs 112 illuminate a surgical site and provide illumination for the optical system and display monitors coupled with the first and second optic tubes 110A, 110B. As a result, the hand piece 100 may be operated remotely by medical personnel using the electronics and control systems as disclosed herein. The medical personnel may view the surgical site and visually monitor an operation by looking through one or more video monitors.

Figure 2:
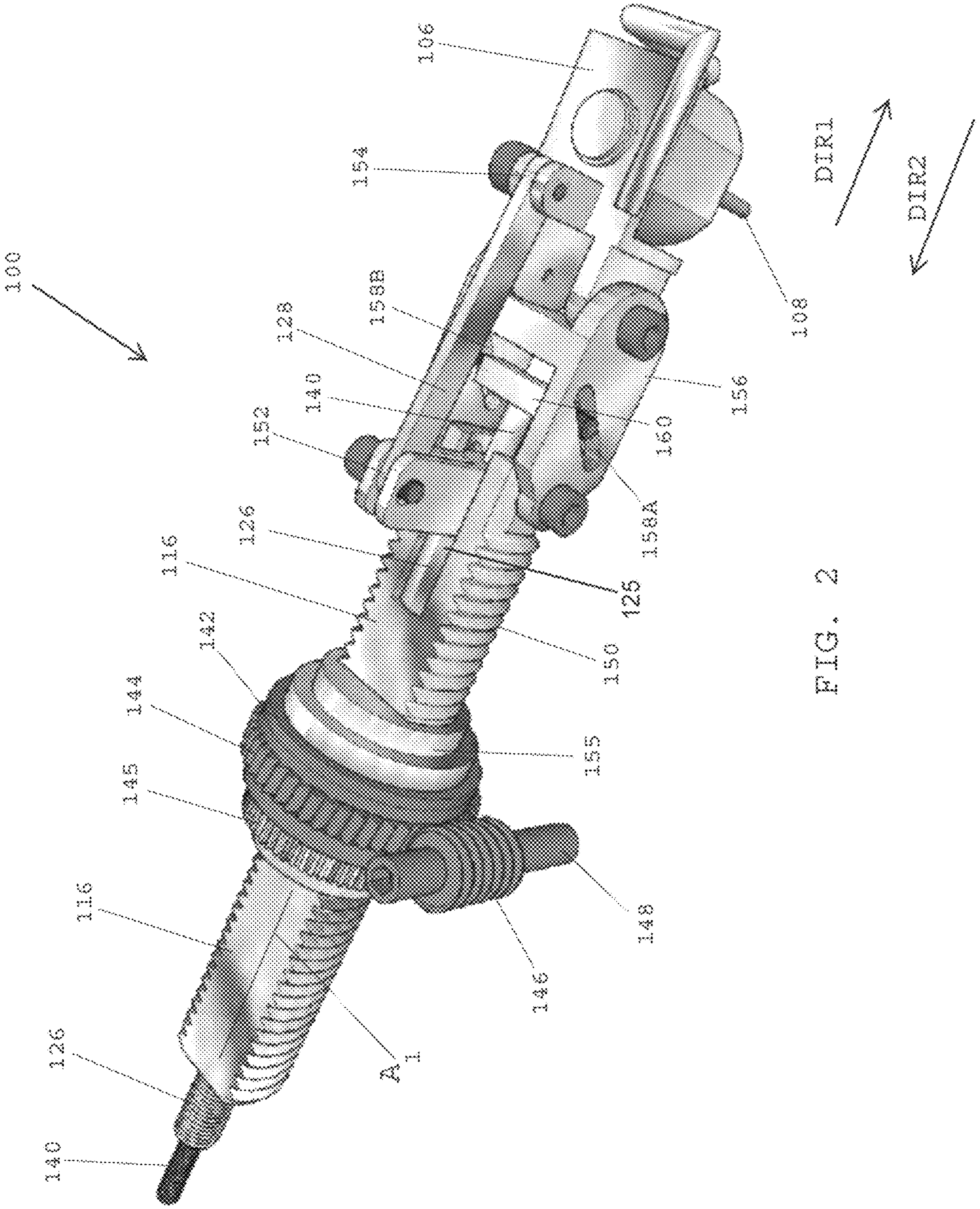
FIG. 2 is a perspective view of components that are located at the distal end of the hand piece shown in FIGS. 1A-1F including a turbine housing, a drill bit projecting from an underside of the turbine housing, a first shaft adapted to extend, retract, and roll the turbine housing, a second shaft adapted to tilt the turbine housing, and a third shaft for adjusting the vertical height of the turbine housing, in accordance with one embodiment of the present patent application.
Figure 3:
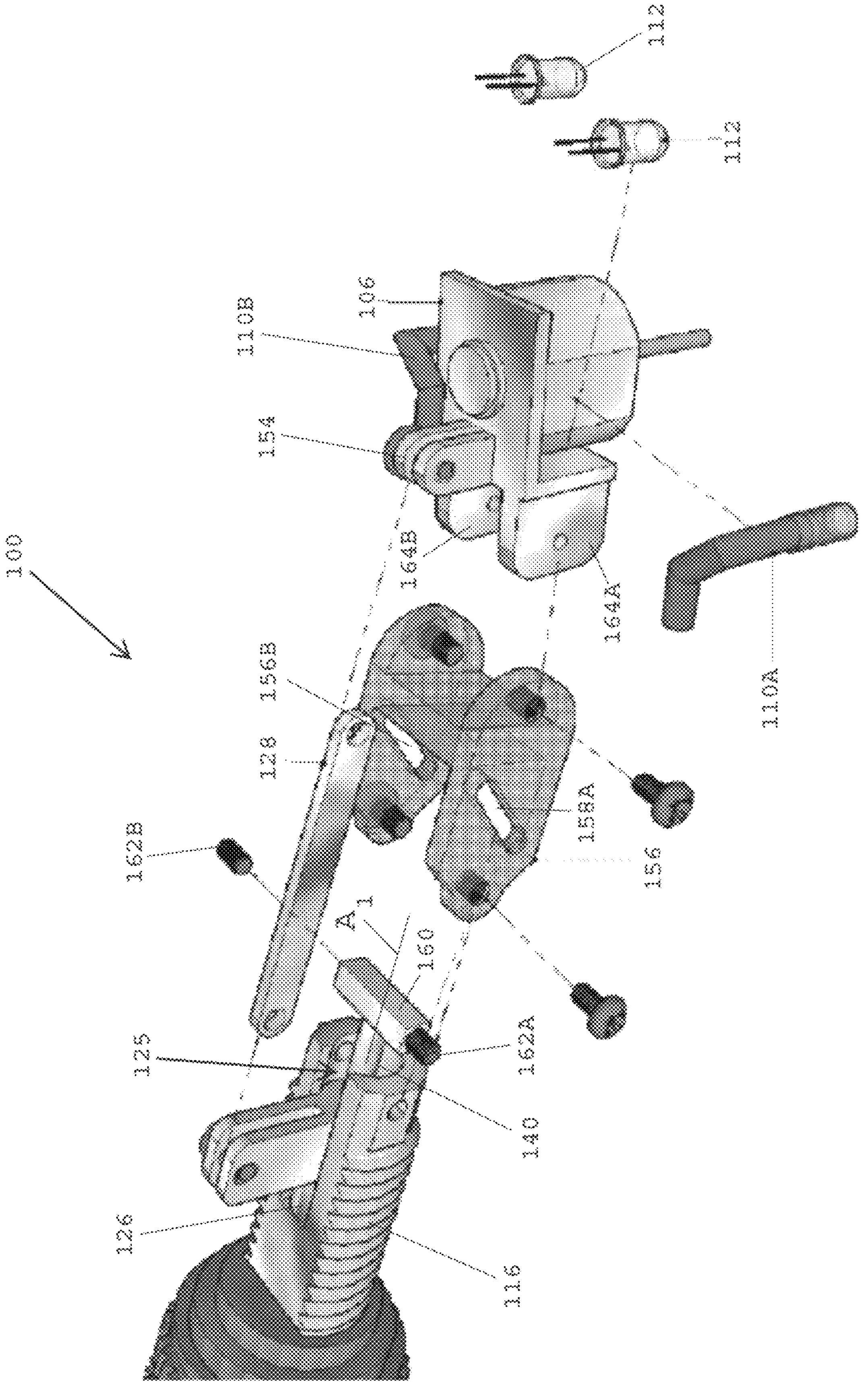
FIG. 3 is a partially exploded view of a distal end of a hand piece of a robotic system for performing a dental procedure including the turbine housing, the drill bit, the first shaft, the second shaft, and the third shaft shown in FIG. 2, in accordance with one embodiment of the present patent application.
Figure 4:
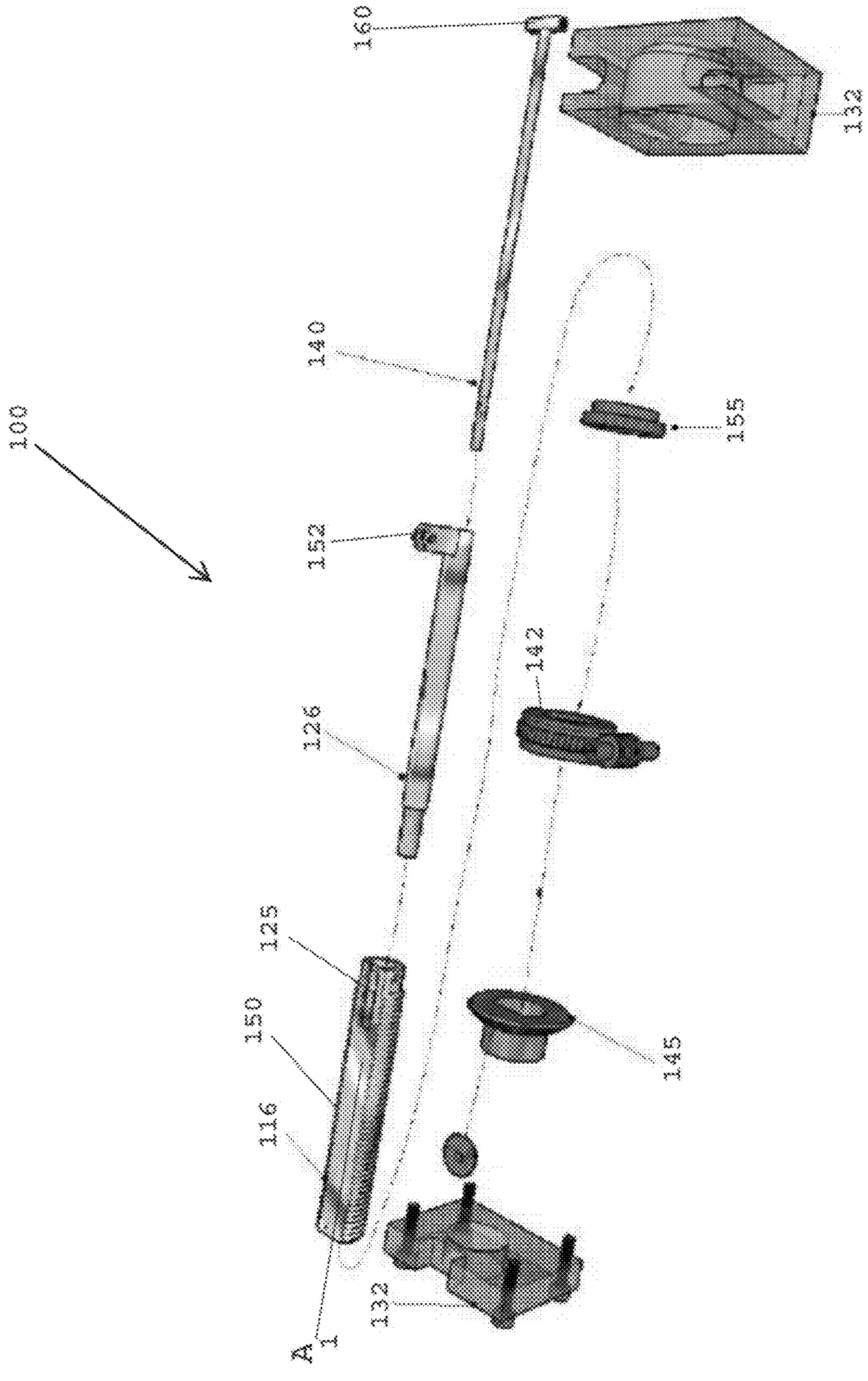
FIG. 4 is an exploded view of the distal end of the hand piece shown in FIG. 3 including the first shaft, the second shaft, and the third shaft shown in FIGS. 2 and 3.

Referring to FIGS. 2-4, in one embodiment, the hand piece 100 preferably includes the first shaft 116, the second shaft 126 that is disposed within an elongated conduit of the first shaft 116, and a third shaft 140 that is disposed within an elongated conduit of the second shaft 126. In one embodiment, the first shaft 116 has a longitudinal axis $A_1$ and the first, second and third shafts 116, 126, and 140 are free to move independently of one another along the longitudinal axis $A_1$. In one embodiment, the first, second and third shafts 116, 126, 140 have distal ends that are coupled with the turbine housing 106 for moving the turbine housing so as to position the drill bit 108 (FIG. 2) at a preferred orientation for drilling a tooth.

In one embodiment, the hand piece 100 preferably includes a first gear 142 having external teeth 144 that are adapted to engage a pinion gear 146 that is coupled with a vertical shaft 148, which, in turn, has an upper end that is connected with the first motor 114 (FIG. 1A) of the robotic system. In one embodiment, the first gear 142 has internal teeth that engage external teeth 150 provided on an outer surface of the first shaft 116. In one embodiment, the first motor 114 (FIG. 1A) may be activated for rotating the vertical shaft 148 and the pinion gear 146 that is mounted on the vertical shaft 148. As the pinion gear 146 rotates, the external teeth of the pinion gear preferably engage the external teeth 144 on the first gear 142 for rotating the first gear. As the first gear 142 rotates, the internal teeth of the first gear engage the external teeth 150 on the first shaft 116 for extending the first shaft distally in the direction designated DIR1. In one embodiment, the first motor 114 (FIG. 1A) may be activated to rotate the first gear 142 in an opposite direction for retracting the first shaft 116 in the proximal direction designated DIR2.

In one embodiment, the hand piece 100 preferably includes a second gear 145 that is coupled with the first shaft 116 for selectively rotating (i.e., rolling) the first shaft about the longitudinal axis $A_1$ of the first shaft 116. In one embodiment, the second gear 145 is coupled with the second motor 118 (FIG. 1A) of the hand piece. In one embodiment, the second motor may be activated for rolling the first shaft 116 about its longitudinal axis, which, in turn, rolls the turbine housing 106 that is coupled with the distal end of the first shaft.

In one embodiment, the hand piece 100 preferably includes the second shaft 126, which may be extended and retracted for changing the angle (i.e., tilt) of the turbine housing 106. In one embodiment, the distal end of the second shaft preferably includes an attachment flange 152 that is pivotally connected with a proximal end of the pivot lever 128. In one embodiment, the distal end of the pivot lever 128 is pivotally connected with an attachment flange 154 that is provided on the turbine housing 106. In one embodiment, the second shaft 126 is coupled with the fourth motor 124 (FIG. 1A) of the hand piece 100.

In one embodiment, the fourth motor 124 (FIG. 1A) of the hand piece 100 may be activated for extending the second shaft 126 in the distal direction designated DIR1. As the second shaft 126 moves distally, the linkage between the distal end of the second shaft 126 and the pivot lever 128 tilts the turbine housing 106 downwardly for changing the angle of the turbine housing. In one embodiment, the fourth motor 124 (FIG. 1A) may be moved in an opposite direction for retracting the second shaft 126 in the proximal direction designated DIR2 for pulling the pivot lever 128 in a proximal direction for tilting the turbine housing 106 upwardly for changing the angle of the turbine housing 106. Thus, the second shaft 126 may be selectively extended and retracted for tilting the turbine housing 106 up and down to place the turbine housing in a preferred orientation for performing a drilling operation.

In one embodiment, the hand piece 100 preferably includes a vertical control housing 156 that is pivotally coupled with a distal end of the first shaft 116 and a proximal end of the turbine housing 106. The vertical control housing 156 preferably includes a pair of diagonal slots 158A, 158B that are adapted to receive a T bar 160 that is secured to the distal end of the third shaft 140. In one embodiment, the fifth motor 130 (FIG. 1A) may be activated for extending the third shaft 140 in the distal direction designated DIR1. As the third shaft 140 moves distally, the T bar 160 at the distal end of the third shaft 140 slides through the diagonal slots 158A, 158B for moving the turbine housing 106 in the direction indicated DOWN in FIG. 1B, thereby adjusting the vertical position of the turbine housing 106 along the axis $A_2$ (FIG. 1B).

In one embodiment, the fifth motor 130 (FIG. 1A) may be moved in an opposite direction for retracting the third shaft 140 in a direction designated DIR2 for moving the T bar 160 toward the proximal end or lower ends of the diagonal openings 158A, 158B for moving the turbine housing 106 in the direction designated UP in FIG. 1B, thereby adjusting the vertical position of the turbine housing 106 along the axis $A_2$ (FIG. 1B).

FIGS. 3 and 4 show exploded views of the distal end of the hand piece 100 including the first shaft 116, the second shaft 126, and the third shaft 140.

In one embodiment, the first shaft 116 has an elongated conduit 125 that is adapted to receive the second shaft 126, whereby the second shaft 126 may move (e.g., slide) distally and proximally relative to the first shaft 116 along the longitudinal axis $A_1$ of the first shaft 116.

In one embodiment, the hand piece 100 preferably includes the third shaft 140 that is adapted to be disposed within an elongated conduit formed in the second shaft 126 so that the third shaft 140 may move distally and proximally along the longitudinal axis $A_1$ of the first shaft 116. In one embodiment, the first, second, and third shafts 116, 126, 140 are free to move independently of and relative to one another along the longitudinal axis $A_1$ of the first shaft 116.

In one embodiment, the second shaft 126 desirably has an attachment flange 152 at a distal end thereof that is preferably adapted to be pivotally coupled with the proximal end of the pivot lever 128 (FIGS. 2 and 3). In one embodiment, the distal end of the pivot lever is adapted to be pivotally coupled with an attachment flange 154 provided on the turbine housing 106. In one embodiment, the hand piece 100 preferably includes the vertical control housing 156 having a pair of diagonal slots 158A, 158B that are adapted to receive projections 162A, 162B that project outwardly from outer ends of the T-bar 160, which is secured to the distal end of the third shaft 140. In one embodiment, the proximal end of the vertical control housing 156 is secured (e.g., pivotally secured) to the distal end of the first shaft 116. In one embodiment, the distal end of the vertical control housing is secured (e.g., pivotally secured) to proximal flanges 164A, 164B of the turbine housing 106.

Referring to FIG. 3, in one embodiment, the hand piece 100 preferably includes the first and second optic tubes 110A, 110B that are adapted to capture pictures and/or video at a surgical site and one or more LEDs 112 that are mounted on the turbine housing 106 for providing visibility and/or illumination at the surgical site.

Referring to FIG. 4, in one embodiment, the first shaft 116 preferably includes the elongated conduit 125 that is adapted to receive the second shaft 126 so that the second shaft 126 may slide through the elongated conduit 117 and move distally and proximally along the longitudinal axis $A_1$ relative to the first shaft 116. In one embodiment, the distal end of the second shaft 126 preferably includes the attachment flange 152 that is adapted to be pivotally coupled with a proximal end of the pivot lever 128 (FIGS. 2 and 3).

In one embodiment, the second shaft 126 preferably has an elongated conduit extending along the length thereof that is adapted to receive the third shaft 140. In one embodiment, after the third shaft 140 is received within the elongated conduit of the second shaft 126, the third shaft 140 is adapted to move distally and proximally along the longitudinal axis $A_1$ and relative to the second shaft 126. In one embodiment, the distal end of the third shaft 140 preferably includes a T-bar 160 that is adapted to engage the diagonal openings 158A, 158B of the vertical control housing 156 (FIG. 3).

In one embodiment, the first gear 142 preferably has internal teeth that engage the external teeth 150 provided on the first shaft 116 for moving the first shaft 116 in distal and proximal directions along the axis $A_1$. In one embodiment, the hand piece 100 preferably includes the second gear 145 that is adapted to rotate (i.e., roll) the first shaft 116 about the longitudinal axis $A_1$ of the first shaft. In one embodiment, the hand piece 100 preferably includes the bushing 155 (FIG. 2) that engages the outer surface of the first shaft 116 for controlling the distal and proximal sliding movement of the first shaft 116 and for controlling the rolling of the first shaft 116 about the longitudinal axis $A_1$. In one embodiment, the first gear 142, the second gear 145, and the bushing 155 are contained within the forward housing 132 (FIG. 1B) of the hand piece 100. As shown in FIG. 1B, the forward housing 132 preferably has openings that enable the first, second, and third shafts 116, 126, 140 to pass through the forward housing.

Figure 5A:
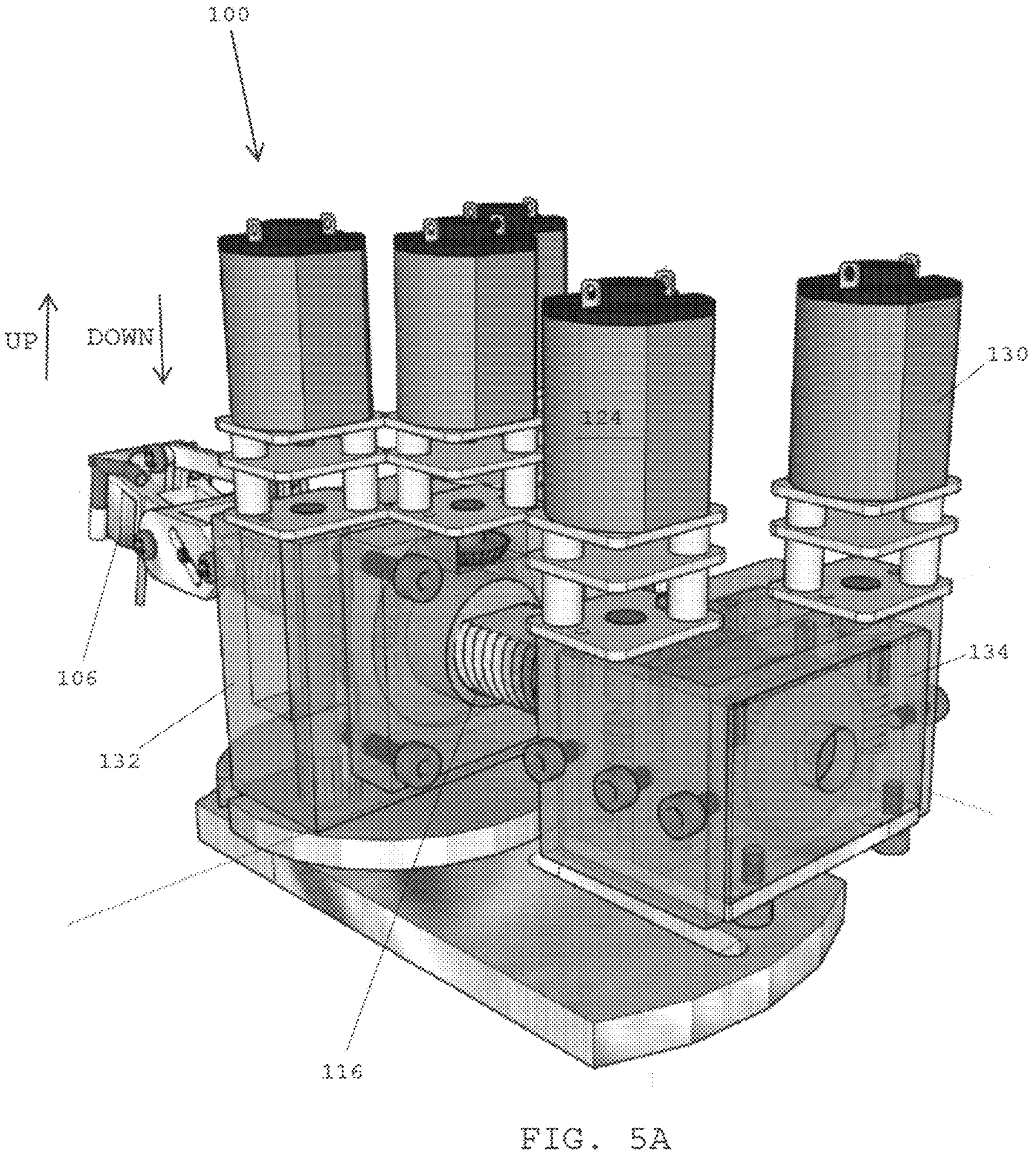
FIG. 5A is a perspective view of a proximal end of the hand piece shown in FIGS. 1A-1F, in accordance with one embodiment of the present patent application.
Figure 5B:
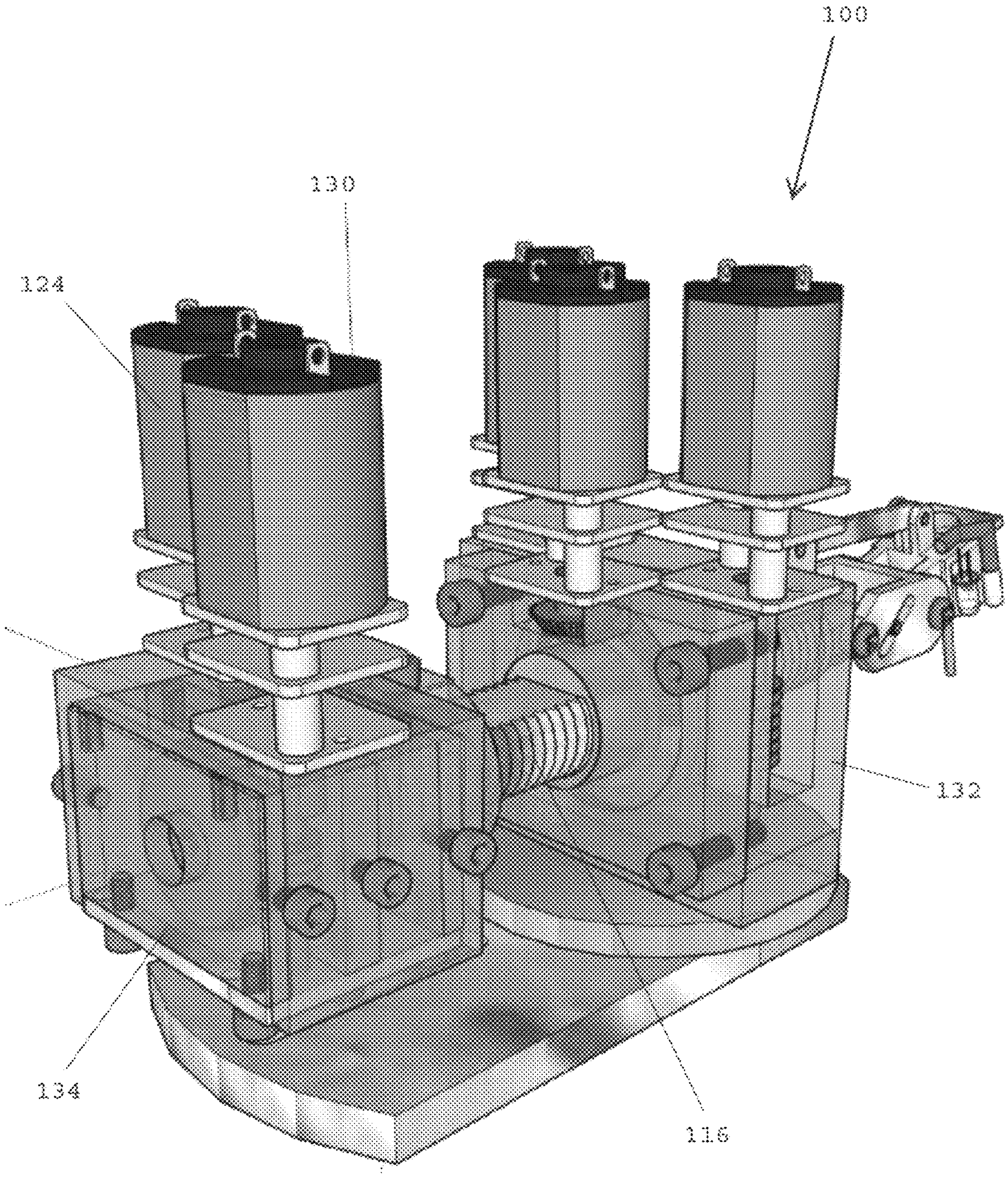
FIG. 5B is another perspective view of the proximal end of the hand piece shown in FIG. 5A.
Figure 5C:
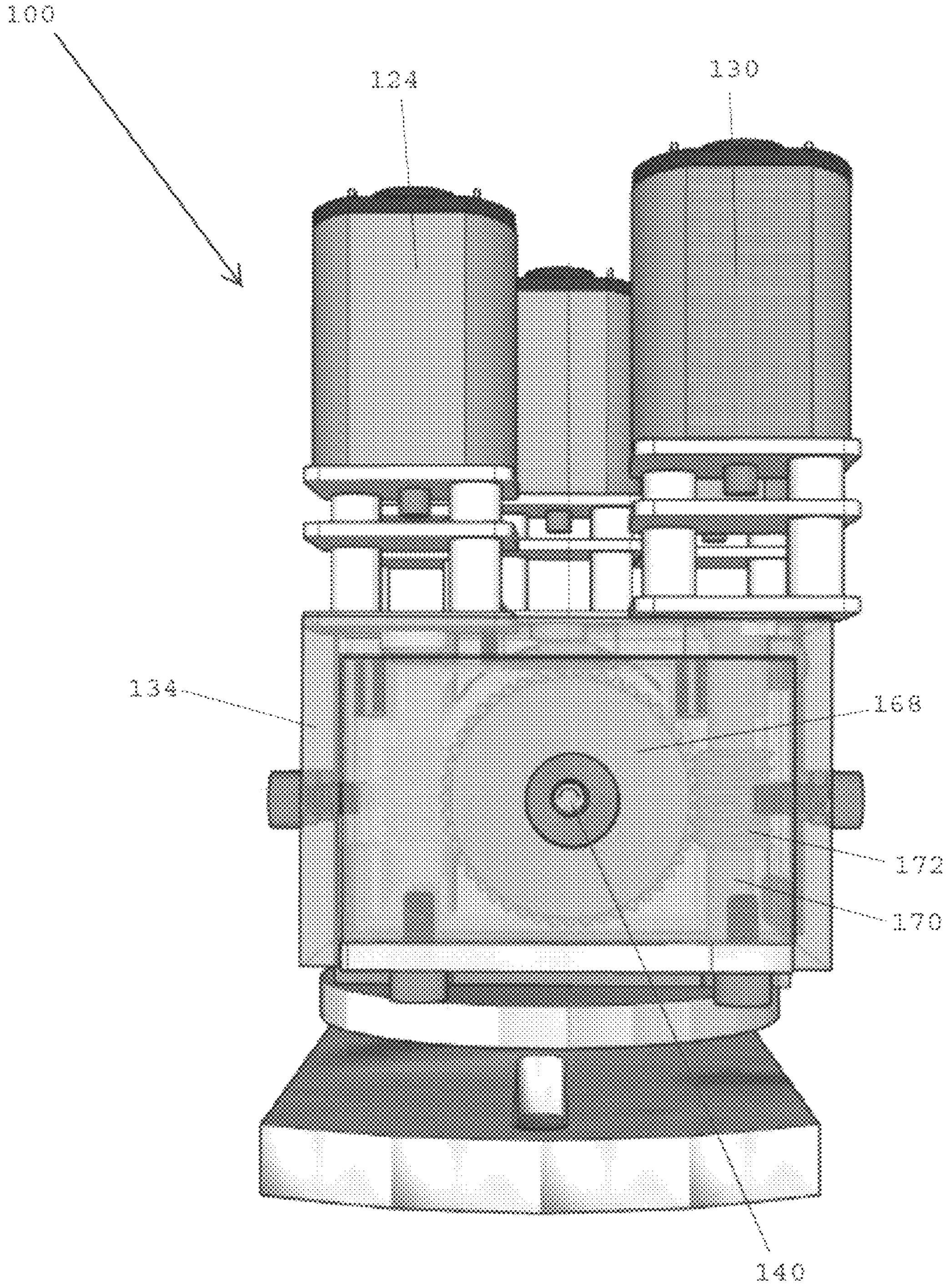
FIG. 5C is a proximal end view of the hand piece shown in FIGS. 5A and 5B.

Referring to FIGS. 5A-5C, in one embodiment, the hand piece 100 preferably includes the rear housing 134 that is coupled with a proximal end of the first shaft 116, and that contains proximal ends of the second and third shafts. The fourth and fifth motors 124, 130 are mounted on (e.g., atop) the rear housing 134 and are adapted to move with the rear housing 134 as it moves distally and proximally relative to the forward housing 132. In one embodiment, the fourth motor 124 is preferably coupled with the second shaft 126 (FIG. 4), which is adapted to move in distal and proximal directions for changing the angle (i.e., tilt) of the turbine housing 106. The fifth motor 130 is preferably coupled with the third shaft 140 (FIG. 4) for changing the vertical height of the turbine housing 106 (i.e., moving the turbine housing up and down along the axis $A_2$ shown in FIG. 1B).

Referring to FIG. 5C, in one embodiment, the rear housing 134 contains a vertical control gear 168 that is coupled with the fifth motor 130 via a vertical shaft 170 and a pinion gear 172. In one embodiment, when the fifth motor 130 is activated, the vertical shaft 170 is rotated about its longitudinal axis for rotating the pinion gear 172, which engages external teeth on the vertical adjustment gear 168 for rotating the third shaft 140 to selectively extend and retract the third shaft. In one embodiment, when the fifth motor 130 is activated for extending the third shaft 140, the turbine housing 106 is moved down along the axis $A_2$ (FIG. 1B). In one embodiment, when the fifth motor 130 is activated for retracting the third shaft 150, the turbine housing 106 is moved up along the axis $A_2$ (FIG. 1B). Thus, the fifth motor 130 and the linkages and gears between the fifth motor and the third shaft 140 may be utilized for extending and retracting the third shaft for adjusting the vertical height of the turbine housing 106 along the axis $A_2$ shown in FIG. 1B.

Figure 6:
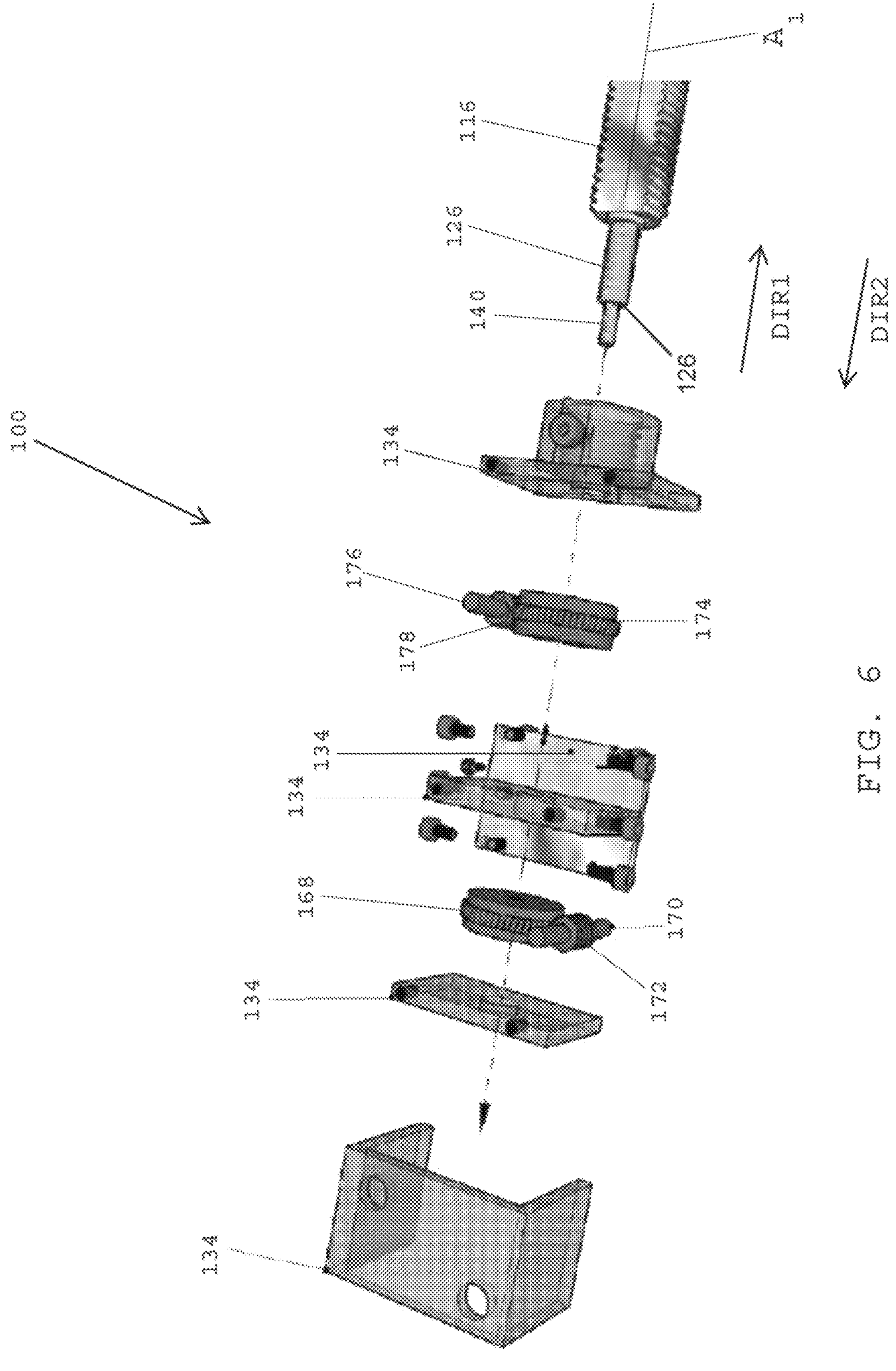
FIG. 6 is an exploded view of the proximal end of the hand piece shown in FIGS. 5A-5C.

Referring to FIG. 6, in one embodiment, the rear housing 134 of the hand piece 100 preferably contains the vertical adjustment gear 168 that is coupled with the vertical shaft 170 and the pinion gear 172, which, in turn, are driven by the fifth motor 130 (FIG. 5C). In one embodiment, the vertical adjustment gear 168 has internal teeth that engage external teeth located at the proximal end of the third shaft 140. As noted above, the vertical adjustment gear 168 is preferably rotated by the fifth motor 130 (FIG. 5C) for selectively extending the third shaft 140 in the distal direction designated DIR1 and retracting the third shaft 140 in the proximal direction designated DIR2.

In one embodiment, the rear housing 134 of the hand piece 100 preferably includes a tilt gear 174 that is coupled with a vertical shaft 176 and a pinion gear 178, which, in turn, are coupled with the fourth motor 124 (FIG. 5C) for changing the angle and/or tilt of the turbine housing 106, which is located at the distal end of the hand piece 100 (FIG. 1A). In one embodiment, the tilt gear 174 preferably has internal teeth that engage external teeth located at the proximal end of the second shaft 126.

In one embodiment, the fourth motor 124 (FIG. 5C) may be activated for rotating the tilt gear 174 in a first direction for extending the second shaft 126 in the distal direction designated DIR1. In one embodiment, the fourth motor may be activated for rotating the tilt gear 174 in an opposite, second direction for retracting the second shaft 126 in the proximal direction designated DIR2.

As noted above, the second shaft 126 is disposed within an elongated conduit that extends along the longitudinal axis $A_1$ of the first shaft 116, and the third shaft 140 is disposed within an elongated conduit that extends along the length of the second shaft 126. The first shaft 116 is adapted to be extended and retracted in the directions DIR1 and DIR2 and also rotate (i.e., roll) about the longitudinal axis $A_1$ of the first shaft 116. The second shaft 126 is adapted to move in distal and proximal directions along the longitudinal axis $A_1$ relative to the first shaft 116. The third shaft 140 is also adapted to move in distal and proximal directions along the longitudinal axis $A_1$ relative to both the first shaft 116 and the second shaft 126.

Figure 7A:
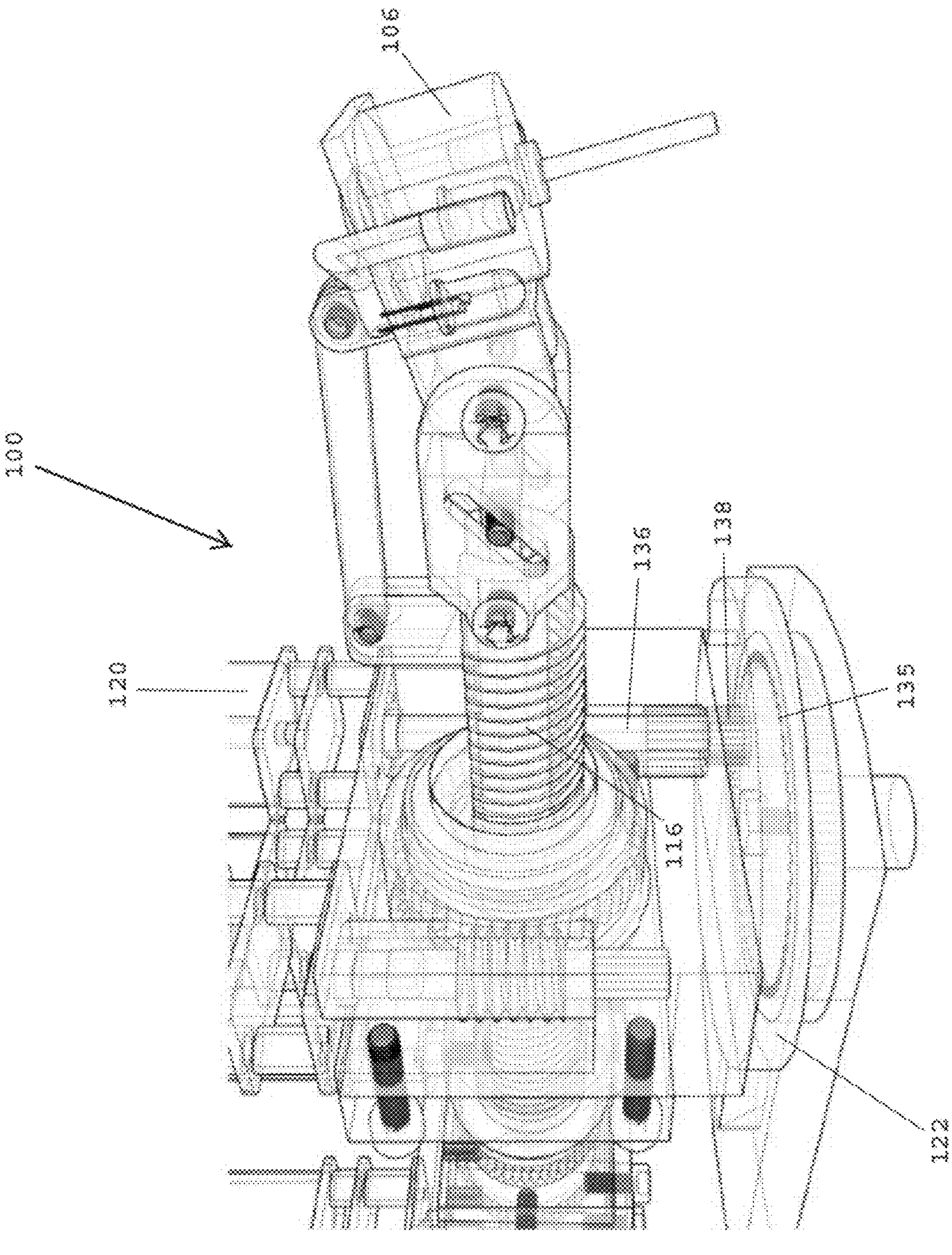
FIG. 7A is a perspective view of a distal end of a hand piece of a robotic system for performing a dental procedure including a turret that is adapted to pan a turbine housing and a drill bit to the left and right, in accordance with one embodiment of the present patent application.
Figure 7B:
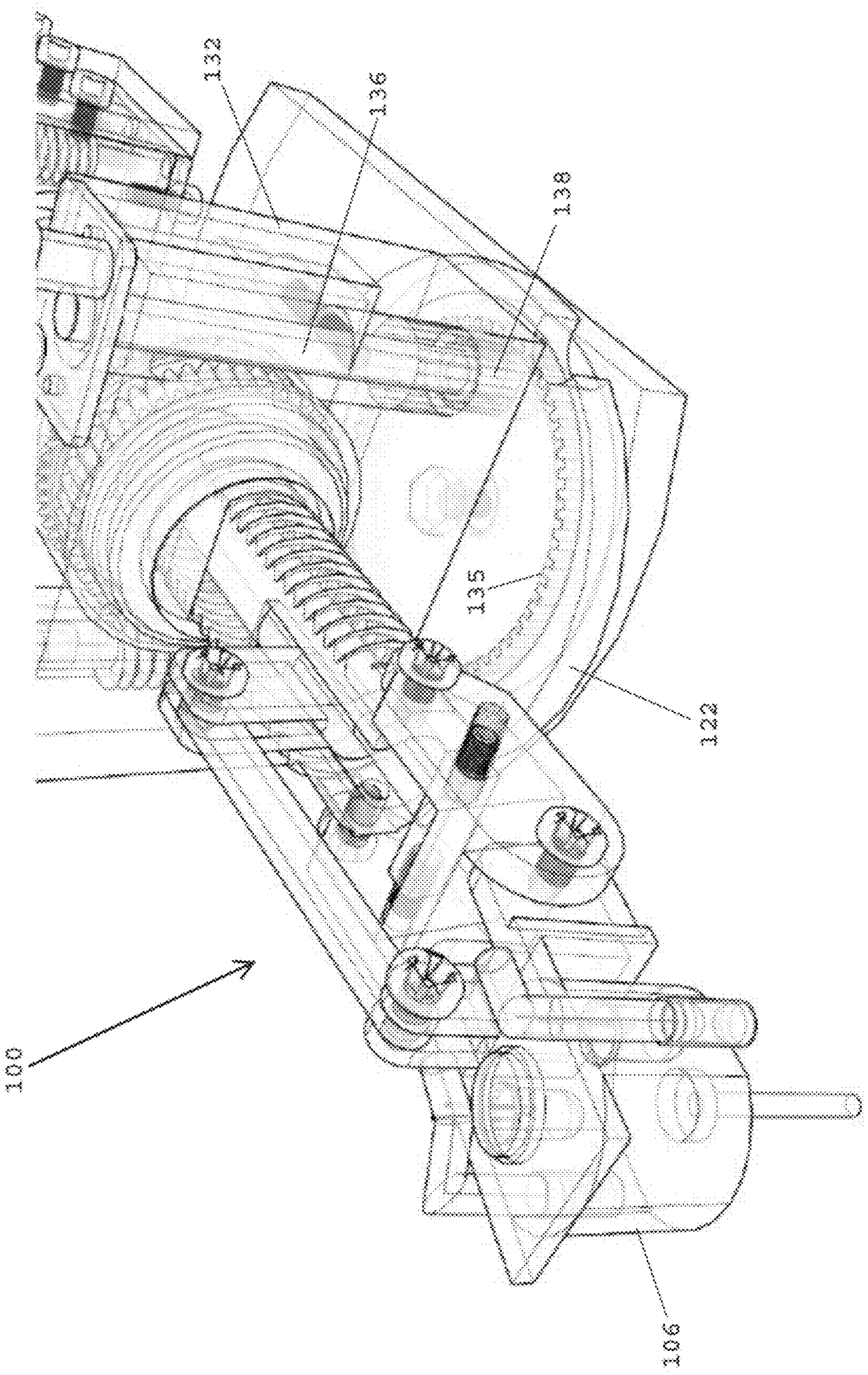
FIG. 7B is another perspective view of the distal end of the hand piece shown in FIG. 7A including the turret, the turbine housing and the drill bit.
Figure 7C:
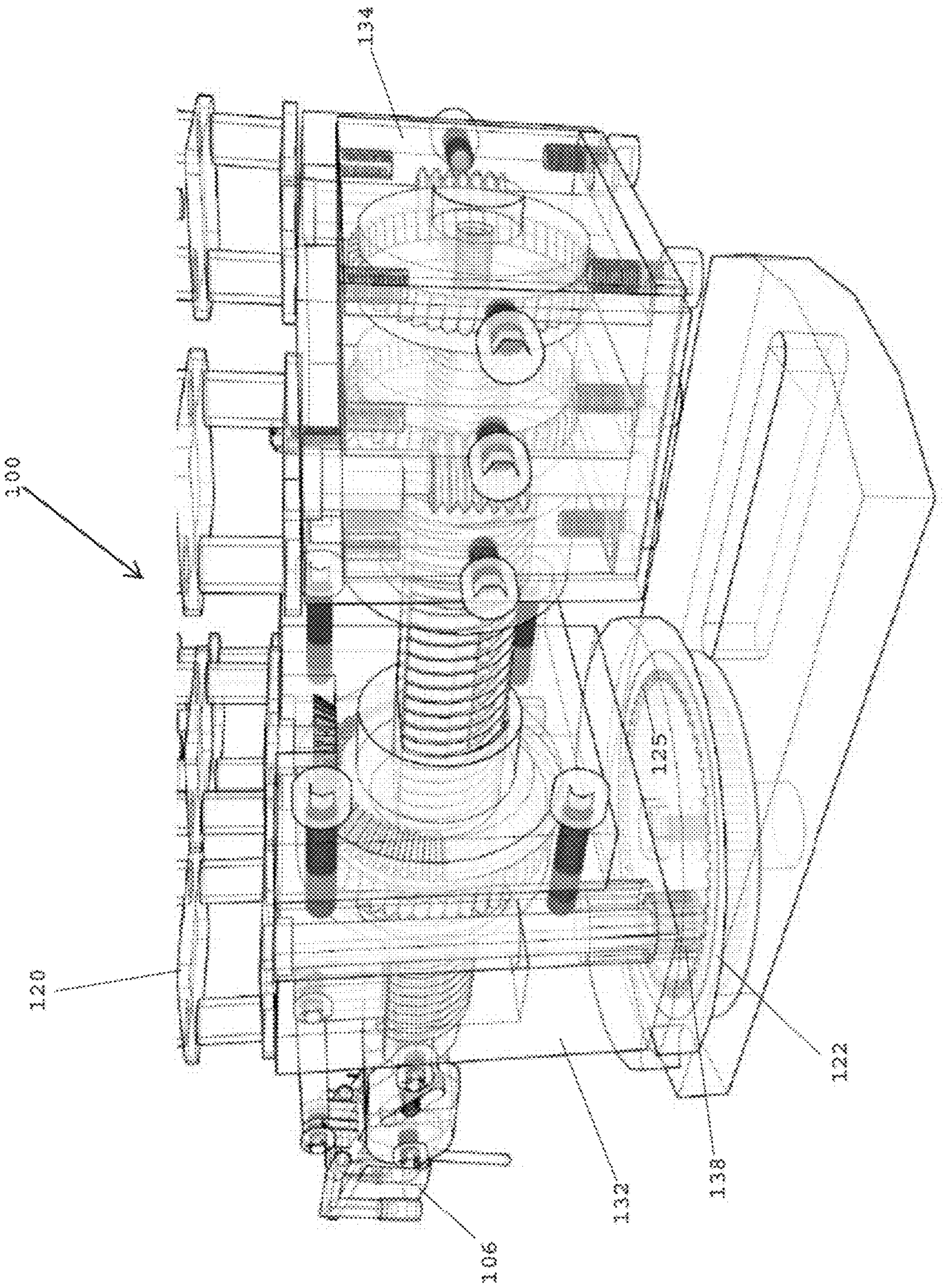
FIG. 7C is a right side view of the hand piece shown in FIGS. 7A and 7B including the turret, the turbine housing and the drill bit.

Referring to FIGS. 7A-7C, in one embodiment, the hand piece 100 preferably includes the turret 122 that is adapted to selectively pan the distal end of the first shaft 116 and the turbine housing 106 to the left and right. In one embodiment, the turret 122 preferably has internal teeth 135 that are adapted to engage external teeth on a pinion gear 138, which is located at a lower end of a vertical shaft 136. The vertical shaft 136 has an upper end that is preferably coupled with the third motor 120 (FIG. 1A) of the hand piece 100. In one embodiment, the third motor 120 may be activated for rotating the vertical shaft 136 about its longitudinal axis, which, in turn, rotates the pinion gear 138, which, in turn, has teeth that engage the internal teeth 135 of the turret 122 for rotating (i.e., panning) the turret base is clockwise and counterclockwise directions. The turret base 122 may be rotated in a first, counterclockwise direction for turning and/or panning the turbine housing 106 to the left. In one embodiment, the third motor 120 may be activated for rotating the turret base 122 in a second, clockwise direction for turning and/or panning the turbine housing 106 to the right. Thus, by activating the third motor 120, the engagement between the pinion gear 138 at the lower end of the vertical shaft 136 and the internal teeth 135 of the turret 122 desirably enables the turbine housing 106 to be automatically moved (i.e., panned) to the left and the right.

Figure 8:
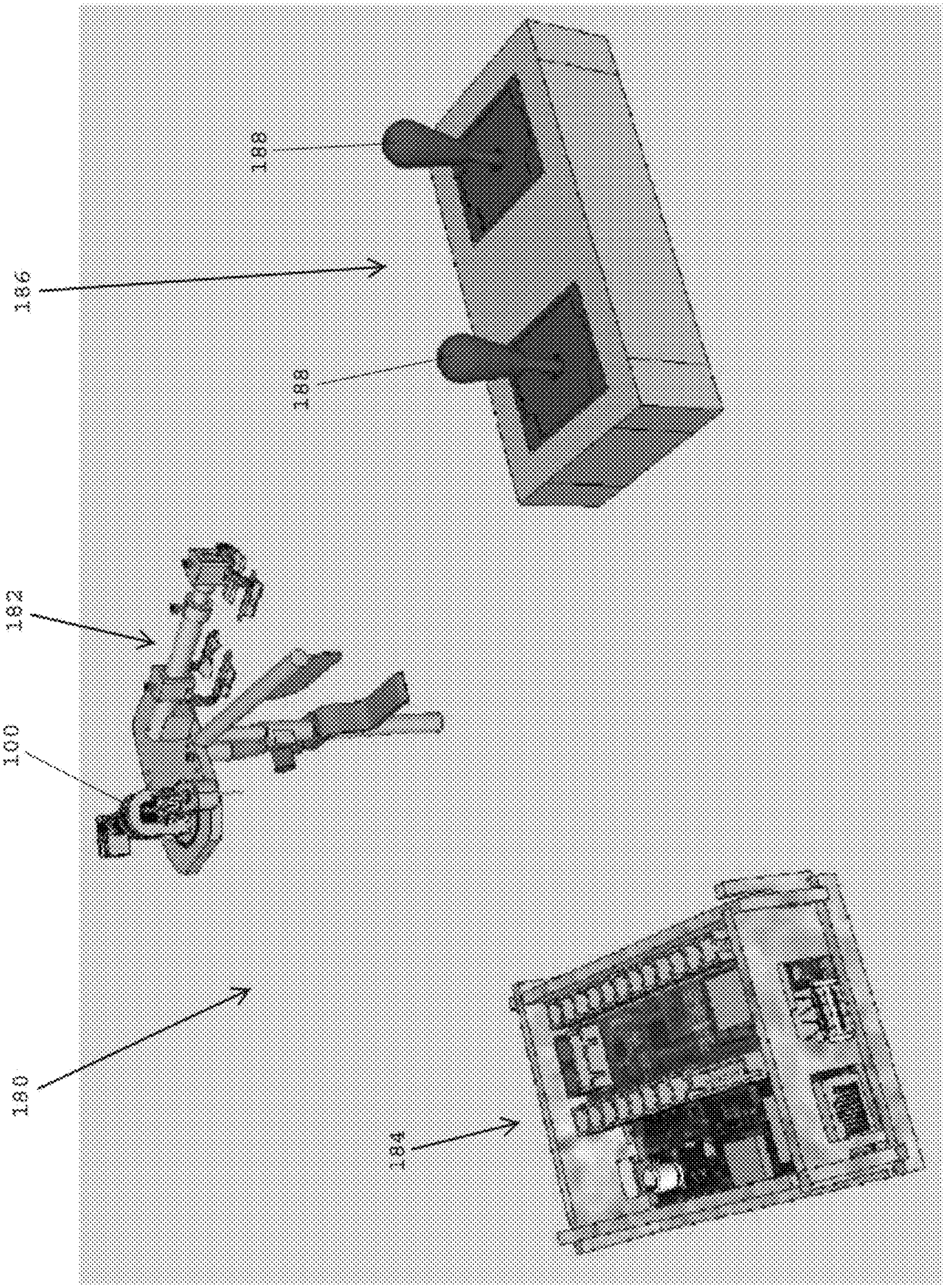
FIG. 8 is a perspective view of a robotic system for performing a dental procedure including a hand piece, an anchoring assembly, a central processing unit, and a system controller, in accordance with one embodiment of the present patent application.

Referring to FIG. 8, in one embodiment, a robotic system 180 for performing a dental procedure preferably includes a hand piece 100 that may be mounted atop an anchoring assembly 182. In one embodiment, the hand piece 100 is adapted to be mounted on the anchoring assembly 182, and the anchoring assembly is adapted to be anchored onto a patient to support the hand piece 100 for performing a dental procedure (e.g., drilling a tooth inside a patient's mouth).

In one embodiment, the robotic system 180 preferably includes a controller 184 that may contain one or more central processing units, software programs, memory devices, communication devices (i.e., wireless, Bluetooth), and electronic components for enabling electronic and remote control of the hand piece 100, which is mounted atop the anchoring assembly 182. In one embodiment, the robotic system 180 preferably includes a remote control device 186, such as one or more joysticks 188, which may be engaged by an operator for electronically and/or remotely controlling the movement of the hand piece 100 including the turbine housing and the drill bit located at the distal end of the hand piece 100. In one embodiment, the joysticks 188 may be engaged for remotely controlling the orientation and/or or position of the turbine housing 106 (FIG. 1A) of the robotic system for extending, retracting, rolling, tilting, elevating, lowering and/or panning the turbine housing.

Figure 9:
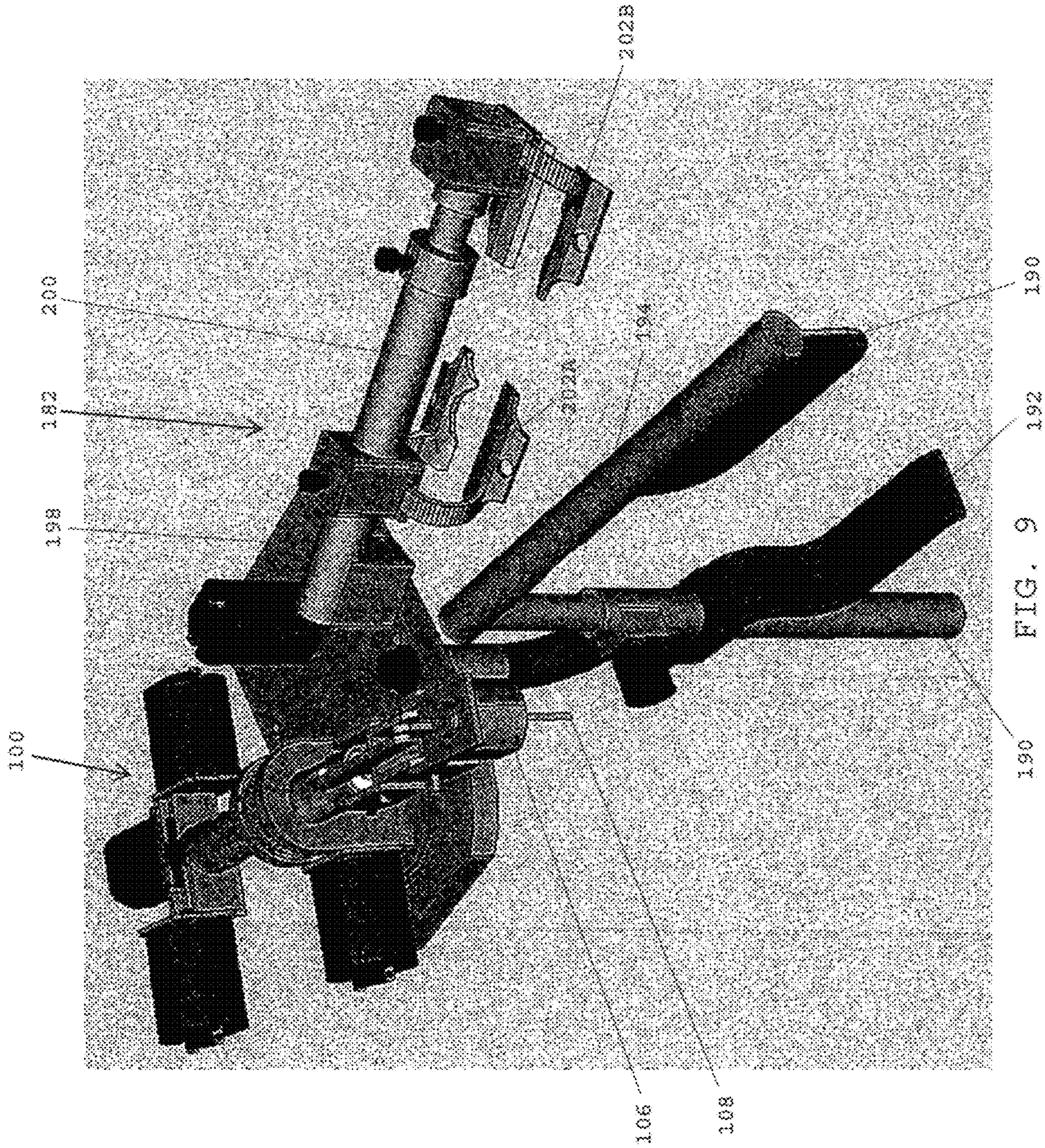
FIG. 9 is a perspective view of a hand piece and an anchoring assembly of a robotic system for performing a dental procedure, in accordance with one embodiment of the present patent application.

Referring to FIG. 9, in one embodiment, the anchoring assembly 182 is preferably adapted to be anchored to a patient and to support the hand piece 100. In one embodiment, the anchoring assembly preferably includes a vertically extending support rod 190 having a chin engaging element 192 mounted thereon. The chin engaging element 192 is preferably adapted to engage an underside of a patient's chin for stabilizing the anchoring assembly 182 after it has been anchored onto a patient.

In one embodiment, the anchoring assembly 182 preferably includes a tongue protector arm 194 coupled with an upper end of the vertical support 190. A free end of the tongue protector arm 194 preferably includes a tongue protector 196 that is adapted to function as a barrier to protect a patient's tongue from the drill bit 108 that projects downwardly from the turbine housing 106. In one embodiment, the tongue protector 196 preferably provides a barrier or guard that is positioned between the drill bit and the patient's tongue to prevent the tongue from being drilled and/or cut by the drill bit.

In one embodiment, the anchoring assembly 182 preferably includes a base plate 198 and a clamp support arm 200 that has a proximal end that is secured to the base plate 198. The clamp support arm 200 is preferably adapted to receive one or more clamps for anchoring the anchoring assembly 182 to a patient. In one embodiment, a pair of clamps 202A, 202B are secured to the clamp support arm 200. The clamps 202A, 202B are adapted to clamp onto the teeth of a patient for anchoring the anchoring assembly 182 to a patient. In one embodiment, the first and second clamps 202A, 202B are adapted to slide along the length of the clamp support arm 200 for enabling medical personnel to modify and/or adjust the exact location of the clamps 202A, 202B relative to the clamp support arm 200.

Figure 10:
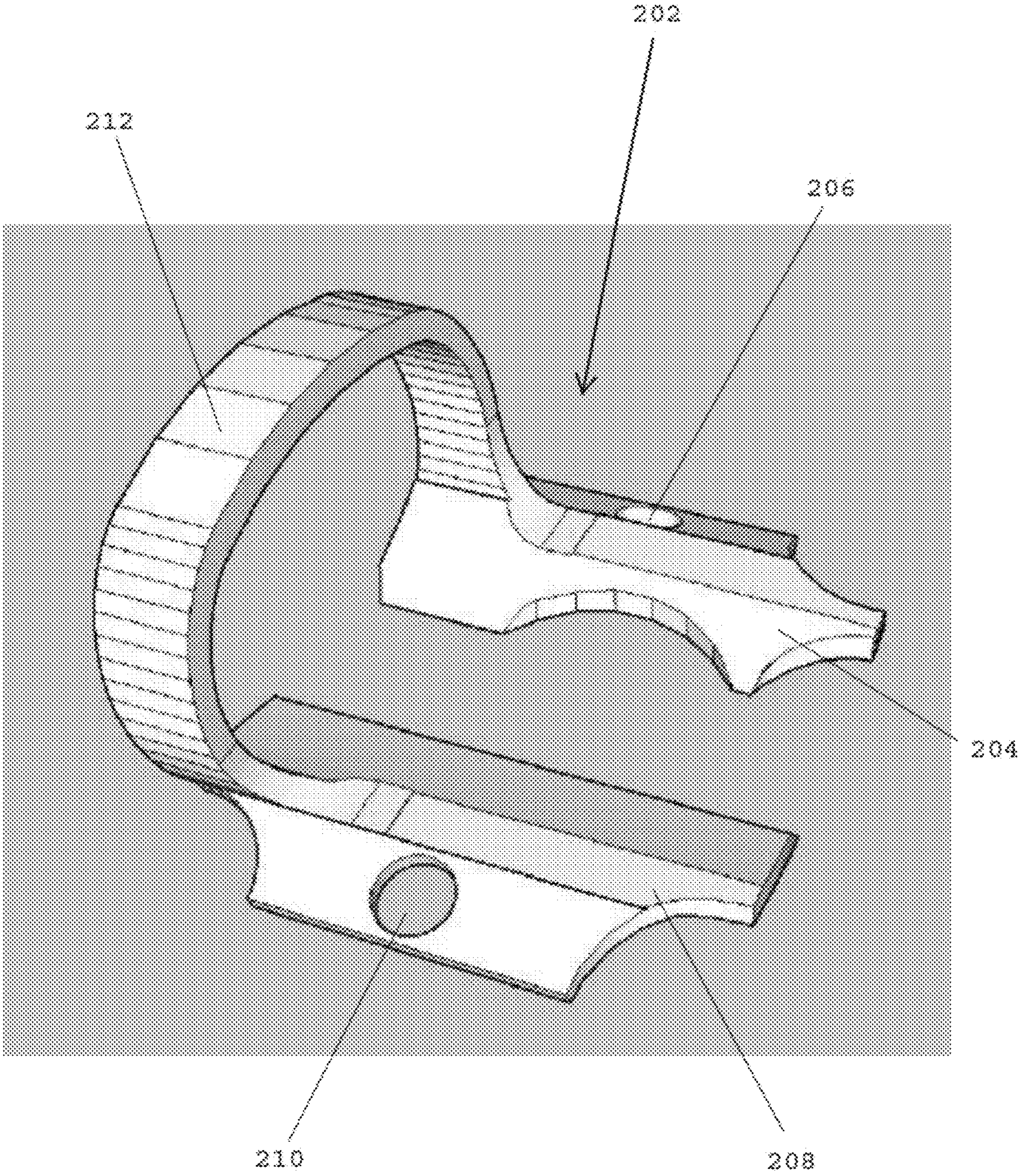
FIG. 10 is a perspective view of a clamp component of the anchoring assembly shown in FIG. 9.

Referring to FIG. 10, in one embodiment, a clamp 202 preferably includes a first flange 204 having a first forceps hole 206 and a second flange 208 having a second forceps hole 210. The first and second flanges 204, 208 preferably oppose one another. In one embodiment, a flexible band 212 desirably interconnects the first and second flanges 204, 208. The opposing surfaces of the first and second flanges 204, 208 preferably have opposing concave surfaces that are adapted to engage the outer surfaces of a tooth. In one embodiment, the forceps holes 206, 210 are adapted to receive the working end of a forceps for moving the first and second flanges 204, 208 away from one another for enabling the clamp 202 to be opened for being positioned over a tooth. After the clamp 202 has been properly positioned over a tooth, the forceps may be removed from the first and second forceps holes 206, 210 for enabling the flexible band 212 to move the opposing flanges 204, 208 back towards one another for providing a clamping force on outer surfaces of a patient's tooth. The clamps 202 preferably clamp the anchoring assembly 182 (FIG. 9) onto a patients teeth for providing a secure base for the hand piece 100 (FIG. 9).

Referring to FIGS. 11A-11D, in one embodiment, the robotic system 180 for performing a dental procedure preferably includes the hand piece 100 mounted atop the attachment base 198 of the anchoring assembly 182. The clamp support arm 200 of the anchoring assembly 182 preferably includes first and second clamps 202A, 202B that are clamped onto the teeth of a patient for providing a stable mount for the robotic system 180.

Figure 11A:
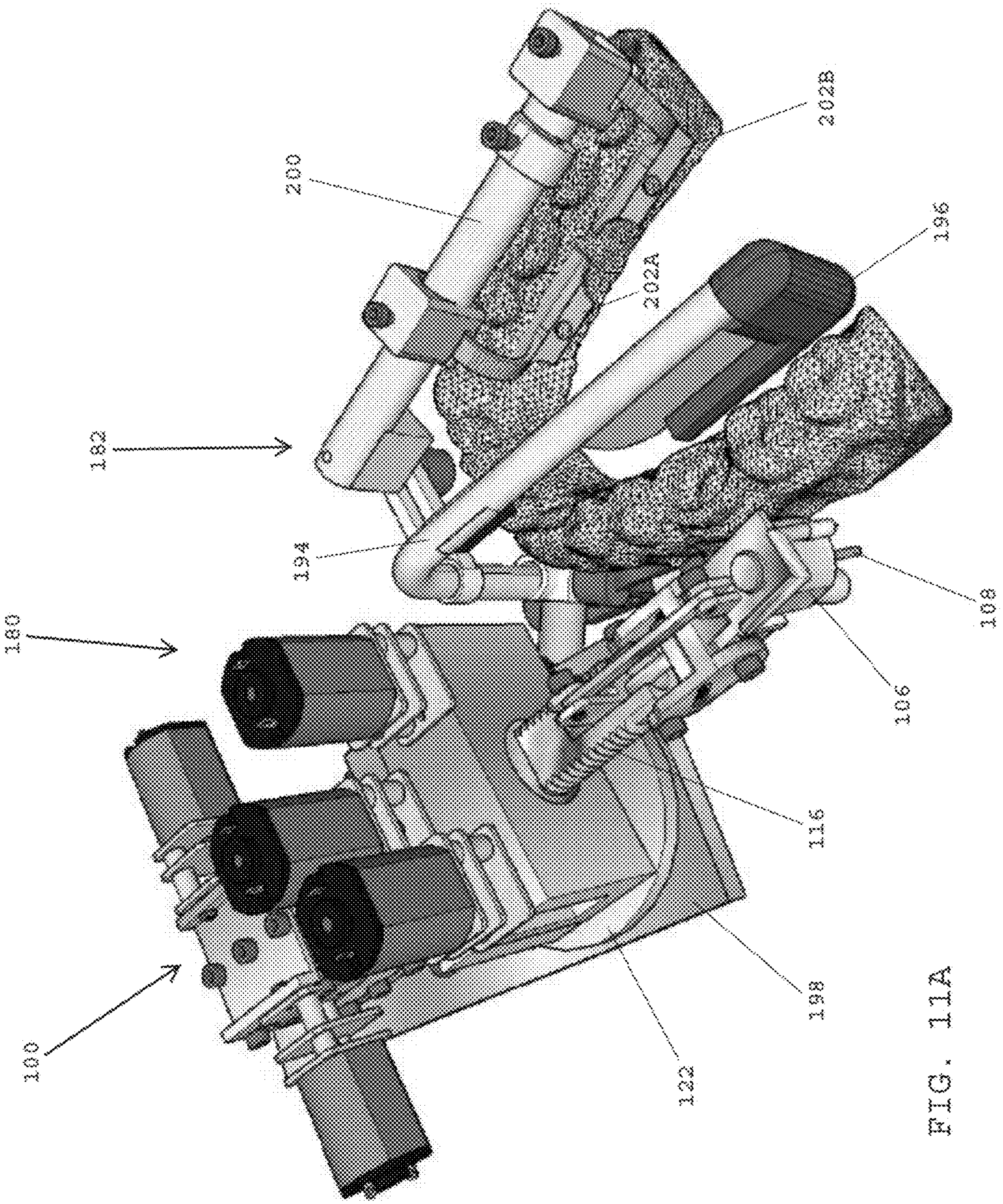
FIG. 11A is a perspective view of a robotic system for performing a dental procedure including a hand piece and an anchoring assembly for anchoring the hand piece to a patient, in accordance with one embodiment of the present patent application.
Figure 11B:
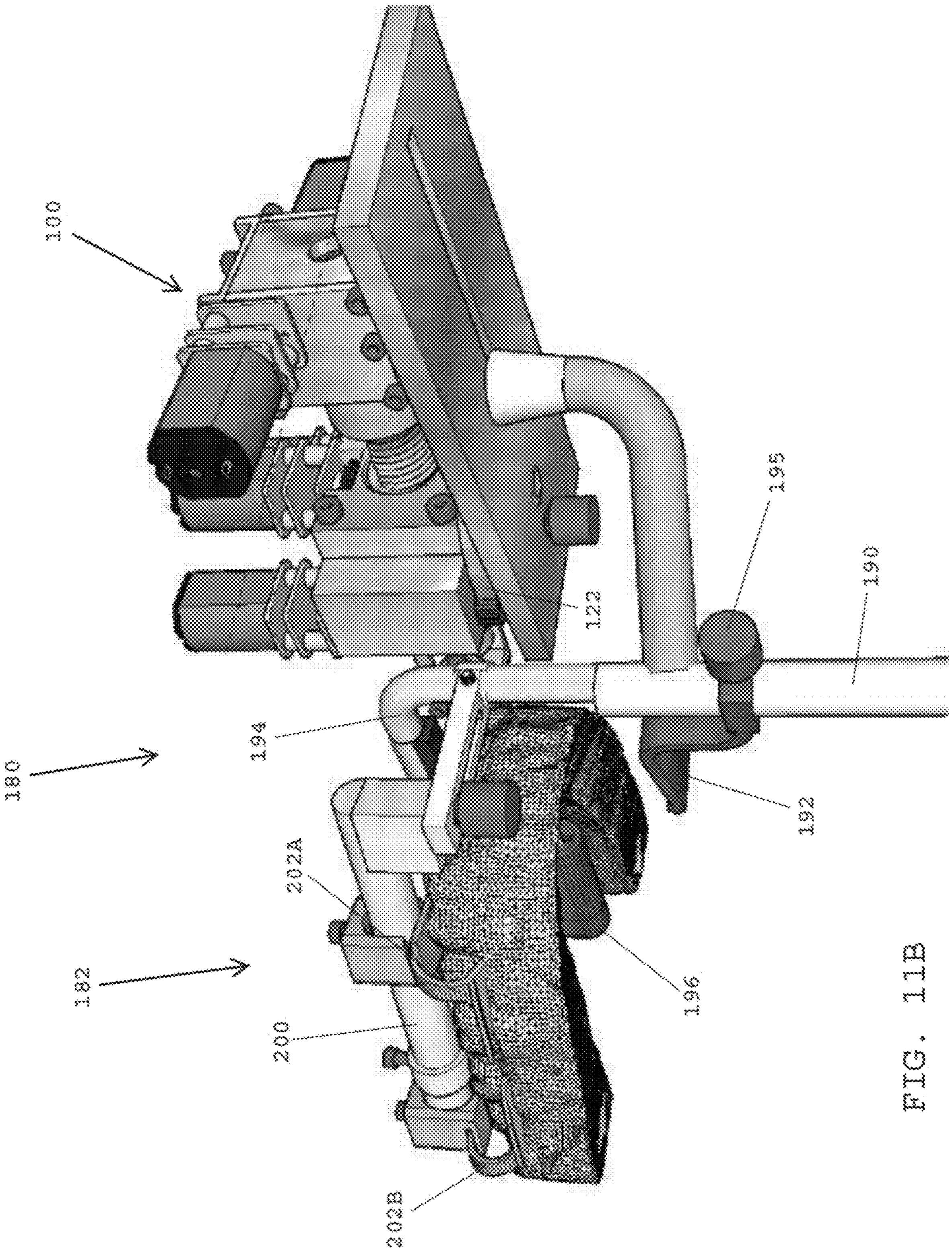
FIG. 11B is a perspective view of a proximal end of the hand piece and the anchoring assembly shown in FIG. 11A.

Referring to FIG. 11B, in one embodiment, the anchoring assembly 182 preferably includes the vertically extending support rod 190 and the chin engaging element 192 mounted thereon. The chin engaging element 192 is preferably adapted to slide up and down the vertically extending support rod 190 for making adjustments for engaging an underside of a patients chin for stabilizing the anchoring assembly 182 on a patient. The anchoring assembly preferably includes a fastener 195, such as a thumb screw, that may be tightened for locking the chin engaging element 192 in place on the vertically extending support rod 190.

Figure 11C:
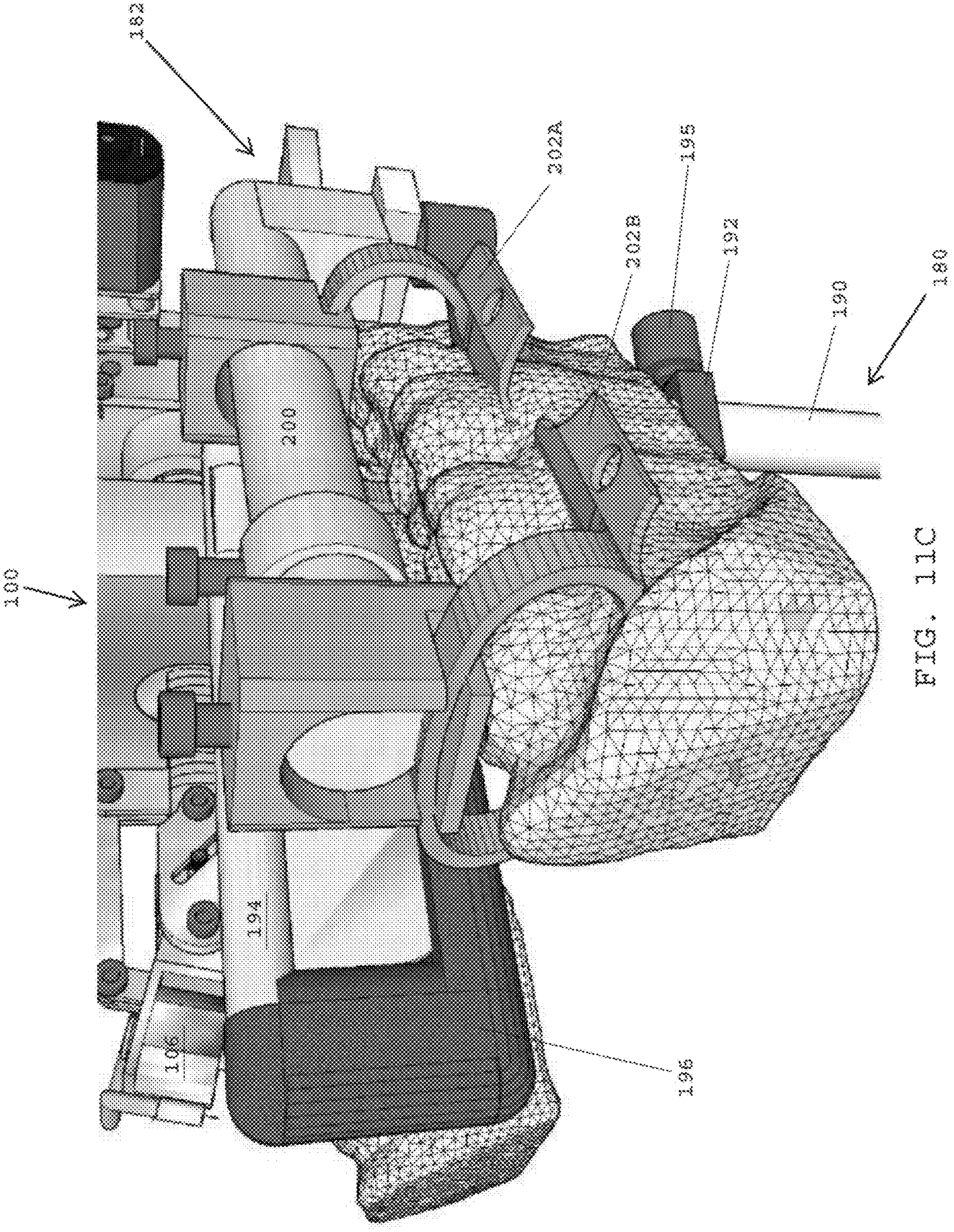
FIG. 11C is a magnified view of a distal end of the anchoring assembly shown in FIGS. 11A and 11B.
Figure 11D:
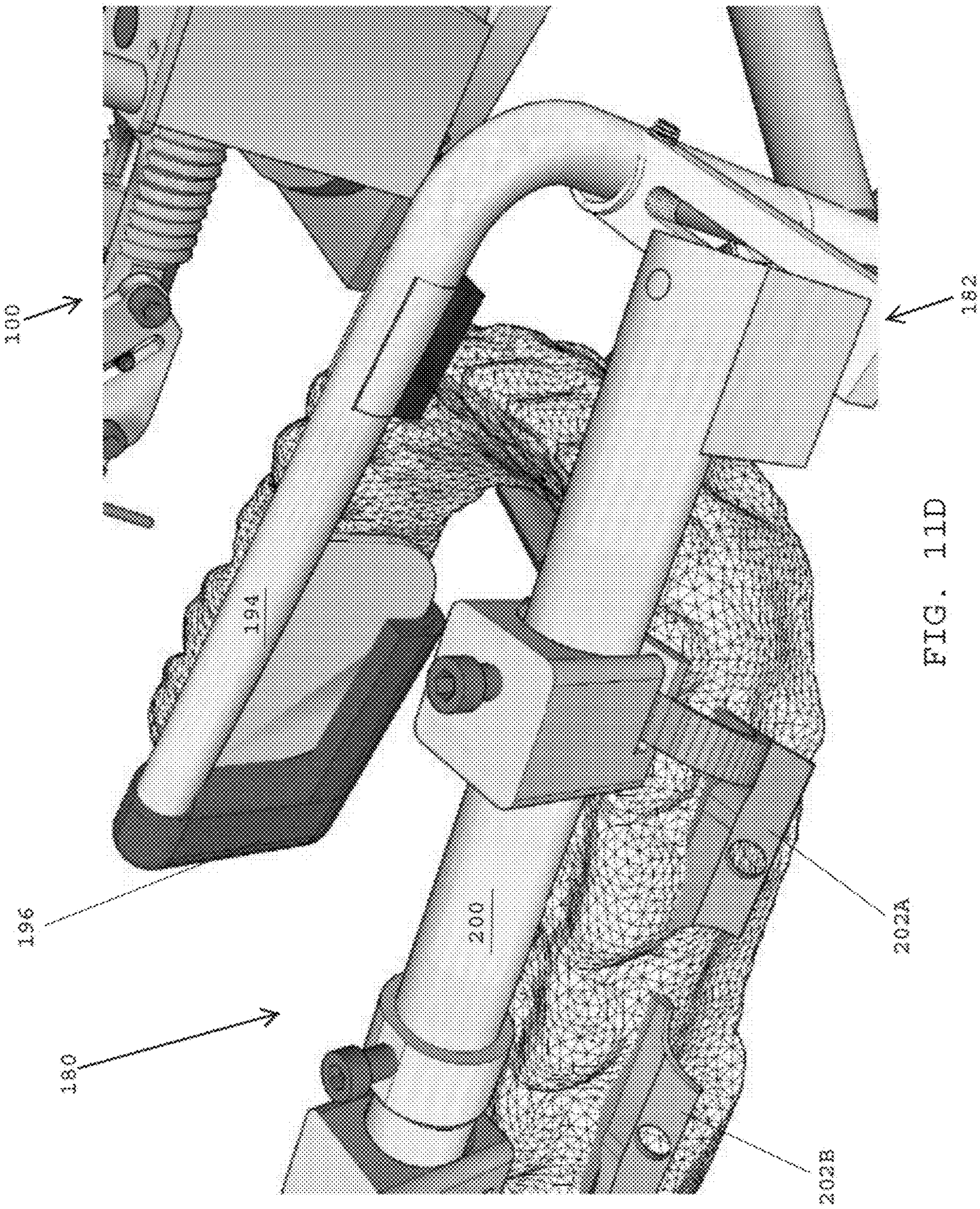
FIG. 11D is a perspective view of a top side of the anchoring assembly shown in FIGS. 11A-11C.

Referring to FIGS. 11A-11D, in one embodiment, the anchoring assembly 182 also preferably includes the tongue protector arm 194 having the tongue protector 196 located at a free end thereof for protecting a patients tongue from the drill bit 108 extending downwardly from the turbine housing 106. As shown in FIGS. 11A, 11C, and 11D, the tongue protector 196 is located between the drill bit 108 and a patient's tongue to protect the tongue from being accidentally cut and/or drilled by the drill bit 108.

In one embodiment, after the robotic system 180 has been mounted onto the patient using the anchoring assembly 182, the control system 184 and the remote control 186 shown and described above in FIG. 8 may be utilized for controlling the movement of the turbine housing 106 and the drill bit 108 for drilling a tooth. As described herein, the control system may be utilized for remotely and robotically extending, retracting, and rotating (i.e., rolling) the first shaft 116 of the hand piece 100. The system controller may also be utilized for changing the angle (i.e., tilt) of the turbine housing 106, and changing the vertical height (i.e., up and down movement) of the turbine housing 106. The control system may also be used for rotating (i.e., panning) the turret 122 to move the turbine housing to the left or the right.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A dental anchoring assembly comprising:

a clamp support arm, a tongue protector arm, and a connector member coupled between said clamp support arm and said tongue protector arm;

one or more tooth clamps coupled with said clamp support arm configured for clamping onto teeth inside a patient's mouth;

a tongue protector associated with said tongue protector arm and adapted for insertion into the patient's mouth adjacent to said one or more tooth clamps;

a base plate upon which a medical device may be mounted, said clamp support arm extending from said base plate in a first plane;

a vertical support arm extending from said base plate in a second plane, generally perpendicular to said first plane;

wherein said tongue protector extends from said vertical support arm in a third plane, generally coplanar or parallel to said first plane; and, said tongue protector associated with said tongue protector arm and adapted for insertion into the patient's mouth engages the patient's tongue on a side opposite said one or more tooth clamps.

2. The dental anchoring assembly of claim 1, wherein said one or more tooth clamps are adapted to be clamped to teeth of the lower mandible.

3. The dental anchoring assembly of claim 1, further comprising a chin engaging element adapted to engage an underside of the patient's chin.

4. The dental anchoring assembly of claim 3, wherein said tongue protector arm is adapted to abut teeth of the lower mandible.

5. The dental anchoring assembly of claim 4, further comprising a vertical support arm extending from said tongue protector arm, said chin engaging element being associated with said vertical support arm.

6. The dental anchoring assembly of claim 1, wherein said clamp support arm and said tongue protector arm form a U-shape with the connector member.

7. The dental anchoring assembly of claim 1, wherein said clamp support arm is linearly extendable.

8. The dental anchoring assembly of claim 1, wherein said tongue protector associated with said tongue protector arm and adapted for insertion into the patient's mouth is adapted to be located between the patient's tongue and a medical device to be used in the patient's mouth on teeth of a second side of a patient's mouth opposite said first side of a patient's mouth.

9. The dental anchoring assembly of claim 8, wherein said one or more tooth clamps are adapted to be clamped to teeth aligned on the lower mandible.

10. The dental anchoring assembly of claim 9, further comprising a chin engaging element adapted to engage an underside of the patient's chin.

11. The dental anchoring assembly of claim 2, wherein said tongue protector arm is adapted to abut one or more teeth on the second side of the patient's mouth.

12. The dental anchoring assembly of claim 10, further comprising a vertical support arm, said chin engaging element being associated with said vertical support arm.

13. The dental anchoring assembly of claim 1, wherein said clamp support arm and said tongue protector arm form a U-shape with the connector member.

14. The dental anchoring assembly of claim 13, wherein said clamp support arm is linearly extendable.

15. The dental anchoring system of claim 1, further comprising a chin engaging element extending from said vertical support arm and adapted to engage an underside of the patient's chin.

16. The dental anchoring assembly of claim 15, wherein said tongue protector arm is adapted to abut one or more of teeth of the patient.

17. The dental anchoring system of claim 1, further comprising a medical device mounted to said base plate, said medical device adapted to perform tasks on a patient's tooth opposite said one or more tooth clamps one side of the patient's mouth.

18. The dental anchoring assembly of claim 1, wherein said clamp support arm is linearly extendable.

* * * * *